United States Patent
Ohashi et al.

(10) Patent No.: US 10,560,639 B2
(45) Date of Patent: Feb. 11, 2020

(54) ENDOSCOPE SYSTEM

(71) Applicant: FUJIFILM Corporation, Tokyo (JP)

(72) Inventors: Eiji Ohashi, Kanagawa (JP); Yoshinori Morimoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/102,756

(22) Filed: Aug. 14, 2018

(65) Prior Publication Data

US 2019/0068864 A1 Feb. 28, 2019

(30) Foreign Application Priority Data

Aug. 31, 2017 (JP) .................................. 2017-166400

(51) Int. Cl.
*H04N 5/235* (2006.01)
*A61B 1/06* (2006.01)
(Continued)

(52) U.S. Cl.
CPC ....... *H04N 5/2354* (2013.01); *A61B 1/00009* (2013.01); *A61B 1/043* (2013.01);
(Continued)

(58) Field of Classification Search
CPC ... A61B 1/00009; A61B 1/043; A61B 1/0638; A61B 1/0653; A61B 1/0684;
(Continued)

(56) References Cited

U.S. PATENT DOCUMENTS 8,858,429 B2 * 10/2014 Mizuyoshi ........... A61B 1/0653
600/118
2012/0078046 A1 * 3/2012 Sasaki ................ A61B 1/00009
600/109
(Continued)

FOREIGN PATENT DOCUMENTS

JP 2014161639 9/2014

OTHER PUBLICATIONS

"Search Report of Europe Counterpart Application", dated Feb. 12, 2019, p. 1-p. 9.

*Primary Examiner* — Christopher S Kelley
*Assistant Examiner* — Kathleen M Walsh
(74) *Attorney, Agent, or Firm* — JCIPRNET

(57) ABSTRACT

Provided is an endoscope system that maintains the hue of an endoscopic image even in a case where a wavelength shift occurs in light for observation.
An endoscope system includes a light source unit including at least one first light source that emits light including two color components with mutually different wavelengths; an image sensor having at least a first element part that has a spectral sensitivity for a first color component and a second element part that has a spectral sensitivity for the second color component out of the two color components of the first light source; and a processor that images an observation object using the light emitted from the at least one first light source of the light source unit and obtains a first signal value of the first color component obtained in the first element part of the image sensor, and a second signal value of the second
(Continued)

color component obtained in the second element part. The processor calculates a signal ratio between the first signal value and the second signal value, and sets the signal ratio to a predetermined set value by changing at least one signal value out of the first signal value and the second signal value.

19 Claims, 10 Drawing Sheets

(51) Int. Cl.
*A61B 1/04* (2006.01)
*H04N 9/04* (2006.01)
*A61B 1/00* (2006.01)
*H04N 5/225* (2006.01)

(52) U.S. Cl.
CPC .......... *A61B 1/0638* (2013.01); *A61B 1/0653* (2013.01); *A61B 1/0684* (2013.01); *H04N 5/2351* (2013.01); *H04N 9/04511* (2018.08); *H04N 2005/2255* (2013.01)

(58) Field of Classification Search
CPC ....... A61B 1/00193; H04N 2005/2255; H04N 5/2351; H04N 5/2354; H04N 9/04511; H04N 13/189; H04N 13/204; G02B 23/2415

USPC ..................................................... 348/45, 70
See application file for complete search history.

(56) References Cited

U.S. PATENT DOCUMENTS

| | | | |
|---|---|---|---|
| 2012/0116159 A1* | 5/2012 | Mizuyoshi | A61B 1/0653 600/109 |
| 2012/0127543 A1* | 5/2012 | Okada | H04N 1/0446 358/475 |
| 2014/0121468 A1* | 5/2014 | Eichenholz | A61B 1/0646 600/249 |
| 2014/0267657 A1* | 9/2014 | Takei | G02B 23/2469 348/68 |
| 2015/0099932 A1* | 4/2015 | Morimoto | H05B 33/0854 600/180 |
| 2016/0106299 A1* | 4/2016 | Kamee | A61B 1/00006 348/67 |
| 2018/0136552 A1* | 5/2018 | Kobayashi | H05B 37/02 |
| 2018/0228355 A1* | 8/2018 | Daidoji | A61B 1/00009 |
| 2018/0279853 A1* | 10/2018 | Daidoji | H04N 13/257 |
| 2018/0289246 A1* | 10/2018 | Tabata | A61B 1/063 |
| 2019/0068864 A1* | 2/2019 | Ohashi | A61B 1/00009 |
| 2019/0110673 A1* | 4/2019 | Ito | A61B 1/0005 |
| 2019/0117041 A1* | 4/2019 | Tanaka | H04N 5/2354 |
| 2019/0117055 A1* | 4/2019 | Ito | A61B 1/0676 |

* cited by examiner

ENDOSCOPE SYSTEM

CROSS-REFERENCE TO RELATED APPLICATIONS

The present application claims priority under 35 U.S.C. § 119 to Japanese Patent Application No. 2017-166400, filed on Aug. 31, 2017. The above application is hereby expressly incorporated by reference, in its entirety, into the present application.

BACKGROUND OF THE INVENTION

1. Field of the Invention

The present invention relates to an endoscope system that acquires an endoscopic image of an observation object using a plurality of kinds of light with different wavelengths, and particularly to an endoscope system that maintains the hue of an endoscopic image even in a case where a wavelength shift occurs in light used for observation.

2. Description of the Related Art

In recent medical care, diagnosis using an endoscope system including a light source device for endoscopes, an electronic endoscope (endoscope), processor device, and the like is widely performed. The light source device for endoscopes generates illumination light to irradiate an observation object. The electronic endoscope captures the observation object irradiated with the illumination light with an image sensor to generate image signals. The processor device performs image processing of the image signals generated by the electronic endoscope to generate an observation image for display on a monitor.

In the related art, in the light source device for endoscopes, lamp light sources, such as a xenon lamp and a halogen lamp, which emit white light as the illumination light, are used. However, in recent years, instead of the lamp light sources, semiconductor light sources such as a laser diode (LD) that emit light of a specific color or a light emitting diode (LED), are used.

For example, an endoscope system including a light source device that supplies illumination light to an endoscope is disclosed in JP2014-161639A. The light source device of JP2014-161639A includes a first semiconductor light source that is constituted of a semiconductor and emits first blue light; a first light source unit that has a fluorescent body which is excited with the blue light to emit fluorescence including a green component and a red component, and that emits white light in which the first blue light transmitted through the fluorescent body and the fluorescence are mixed with each other; a blue light cutoff filter that is disposed on a light path of the white light and cuts the first blue light transmitted through the fluorescent body; a second light source unit having a second semiconductor light source which emits second blue light; a light mixing unit that mixes the second blue light with fluorescence to generate white light in the subsequent stage of the blue light cutoff filter; and a light source controller that controls respective quantities of light of the first and second light source units.

SUMMARY OF THE INVENTION

JP2014-161639A discloses that the hue of an observation region changes in a case where the color balance (light quantity ratio) between fluorescence FL including a G component (green component) and an R component (red component) of the white light and blue light B corresponding to a B component (blue component) changes. In contrast, JP2014-161639A discloses that accurate correction of the color balance is possible because the light quantity control of keeping the light quantity ratio between the fluorescence FL and the blue light B constant due to the configuration of the above-described light source device is performed. In this way, the light quantity control of keeping the light quantity ratio constant is performed in JP2014-161639A. However, in the semiconductor light sources, in addition to fluctuations of the light quantity ratio, a wavelength shift may occur due to a temperature drift caused by emission intensity. The hue of an observation region may change due to the wavelength shift. In this case, it is necessary to perform correction in conformity of the wavelength shift. However, it is not possible to cope with this in the light quantity control of JP2014-161639A.

An object of the invention is to solve the problems based on the aforementioned related art and provide an endoscope system that maintains the hue of an endoscopic image even in a case where a wavelength shift occurs in light for observation.

In order to achieve the above object, the invention provides an endoscope system comprising a light source unit including at least one first light source that emits light including two color components with mutually different wavelengths; an image sensor having at least a first element part that has a spectral sensitivity for a first color component and a second element part that has a spectral sensitivity for the second color component out of the two color components of the first light source; and a processor that images an observation object using the light emitted from at least one first light source of the light source unit and obtains a first signal value of the first color component obtained in the first element part of the image sensor, and a second signal value of the second color component obtained in the second element part. The processor calculates a signal ratio between the first signal value and the second signal value and sets the signal ratio to a predetermined set value by changing at least one signal value out of the first signal value and the second signal value.

It is preferable that the processor calculates a brightness value using at least one of the first signal value or the second signal value of the image sensor, specifies a quantity of light of the first light source on the basis of the brightness value, and sets the signal ratio to a predetermined set value by changing at least one signal value out of the first signal value and the second signal value in accordance with the quantity of light.

It is preferable that the light source unit has at least one second light source that emits light of a color other than the two color components, the image sensor has at least a third element part that has a spectral sensitivity for the light of the color other than the two color components, and the processor obtains a third signal value of the light of the color other than the two color components obtained in the third element part of the image sensor.

It is preferable that the light source unit has one first light source and one second light source, the image sensor has the first element part, the second element part, and the third element part, and the processor obtains the first signal value, the second signal value, and the third signal value that are respectively obtained in the first element part, the second element part, and the third element part of the image sensor.

It is preferable that the processor calculates a brightness value from at least one of the first signal value, the second signal value, or the third signal value of the image sensor, specifies a quantity of light of the first light source on the basis of the brightness value, and sets the signal ratio to a predetermined set value by changing at least one signal value out of the first signal value, the second signal value, and the third signal value in accordance with the quantity of light.

It is preferable that the processor calculates a brightness value from at least one of the first signal value, the second signal value, or the third signal value of the image sensor, specifies a quantity of light of the first light source on the basis of the brightness value, and sets the signal ratio to a predetermined set value by changing at least one signal value out of the first signal value, the second signal value, and the third signal value in accordance with the quantity of light with one signal value among the first signal value, the second signal value, and the third signal value as a reference value.

It is preferable that the light of the color other than the two color components is light showing blue, and, out of the two color components, the first color component is green and the second color component is red.

It is preferable that the light of the color other than the two color components is light showing red, and, out of the two color components, the first color component is blue and the second color component is green.

It is preferable that the light source unit has, as the first light source, a light source that emits light including the first color component showing green and the second color component showing red, or a light source that emits light including the first color component showing blue and the second color component showing green.

It is preferable that the light source unit has, as the first light source, a light source that emits light including the first color component showing green and the second color component showing red, and a light source that emits light including the first color component showing blue and the second color component showing green.

It is preferable that the first light source has a light emitting element that emits excitation light, and a fluorescent body that emits light including the first color component and the second color component with the excitation light.

It is preferable that the first light source has a light emitting diode including an emission spectrum including the first color component and the second color component. It is preferable that the first light source has a light emitting diode having a light emission peak between a peak wavelength of the spectral sensitivity of the first element part and a peak wavelength of the spectral sensitivity of the second element part.

It is preferable that the image sensor has a range where the spectral sensitivity of the first element part and the spectral sensitivity of the second element part overlap each other.

The invention provides an endoscope system including a light source unit including at least one first light source that emits light including two color components with mutually different wavelengths; an image sensor having at least a first element part that has a spectral sensitivity for a first color component and a second element part that has a spectral sensitivity for the second color component out of the two color components of the first light source; and a processor that images an observation object using the light emitted from the at least one first light source of the light source unit and obtains a first signal value of the first color component obtained in the first element part of the image sensor, and a second signal value of the second color component obtained in the second element part, and calculates a signal ratio between the first signal value and the second signal value. In the first light source, a light quantity ratio between the first color component and the second color component changes depending on the quantity of light of the light to be emitted. The processor calculates a brightness value using at least one of the first signal value or the second signal value of the image sensor, specifies the quantity of light of the first light source on the basis of the brightness value, and changes at least one signal value out of the first signal value and the second signal value such that the signal ratio has a predetermined set value in accordance with the quantity of light.

According to the invention, the hue of an endoscopic image can be maintained irrespective of the quantity of light.

DESCRIPTION OF THE PREFERRED EMBODIMENTS

Hereinafter, an endoscope system related to the invention will be described in detail on the basis of a preferable embodiment illustrated in the attached drawings.

In addition, the drawings to be described below are illustrative drawings for describing the invention, and the invention is not limited to the following drawings.

In addition, in the following, "to" showing a numerical range includes numerical values described on both sides thereof. For example, ε being a numerical value α to a numerical value β means that the range of ε is a range including the numerical value α and the numerical value β, and in a case where these are expressed by mathematical symbols, α≤ε≤β is satisfied.

Angles, such as "parallel," include error ranges that are generally allowed in a corresponding technical field unless otherwise specified. The "same" includes error ranges that are generally allowed in a corresponding technical field unless otherwise specified.

Generally, the wavelength of blue is about 445 nm to about 485 nm. For example, a color between blue and green is referred to as bluish green and may be distinguished from blue. However, in an endoscope system 10, there is no need for excessively subdividing the type of color (the name of color) regarding at least light components emitted by individual light sources of the light source unit. For this reason, a color of light having a wavelength of about 440 nm or more and less than about 490 nm is referred to as blue. Additionally, a color of light having a wavelength of about 490 nm or more and less than about 600 nm is referred to as green, and a color of light having a wavelength of about 600 nm or more and less than about 680 nm is referred to as red. Also, a color of visible light having a wavelength of less than "about 440 nm" which is a lower limit of the wavelength of the above-described blue, for example, visible light of about 380 nm or more and less than about 440 nm is referred to as purple, and a color of light which has a wavelength shorter than purple but for which an image sensor 48 has sensitivity is referred to as ultraviolet. Additionally, a color of light which has a wavelength of "about 680 nm" or more that is an upper limit of the wavelength of the above-described red and for which the image sensor 48 has sensitivity is referred to as infrared. Additionally, the term "broadband" means that the wavelength range reaches the wavelength range of a plurality of colors. White means a color of light including at least the light that belongs to the above-described blue or purple, the light that belongs to green, and the light that belongs to red.

First Embodiment

Figure 1:
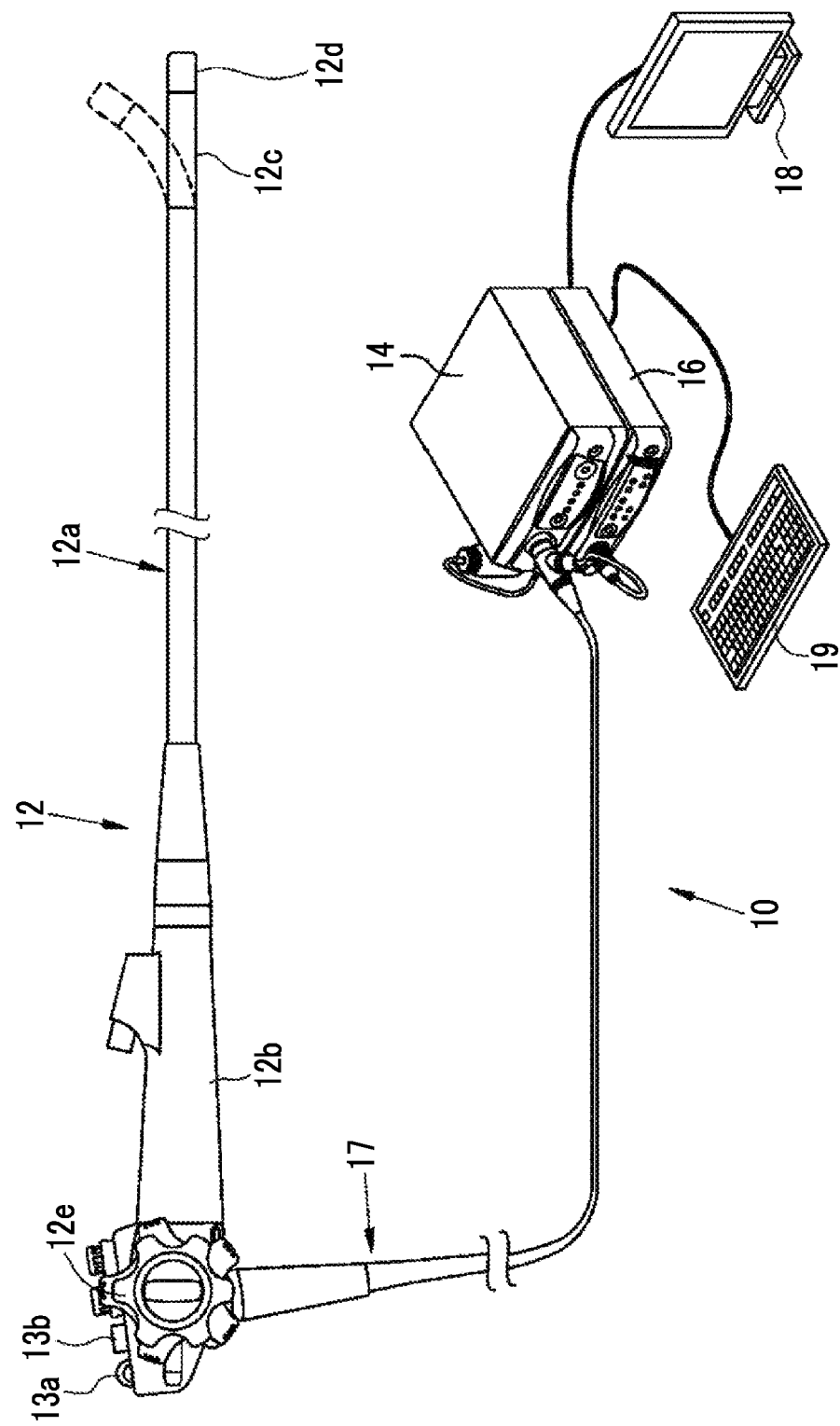
FIG. 1 is a perspective view conceptually illustrating an example of an endoscope system of a first embodiment of the invention.
Figure 2:
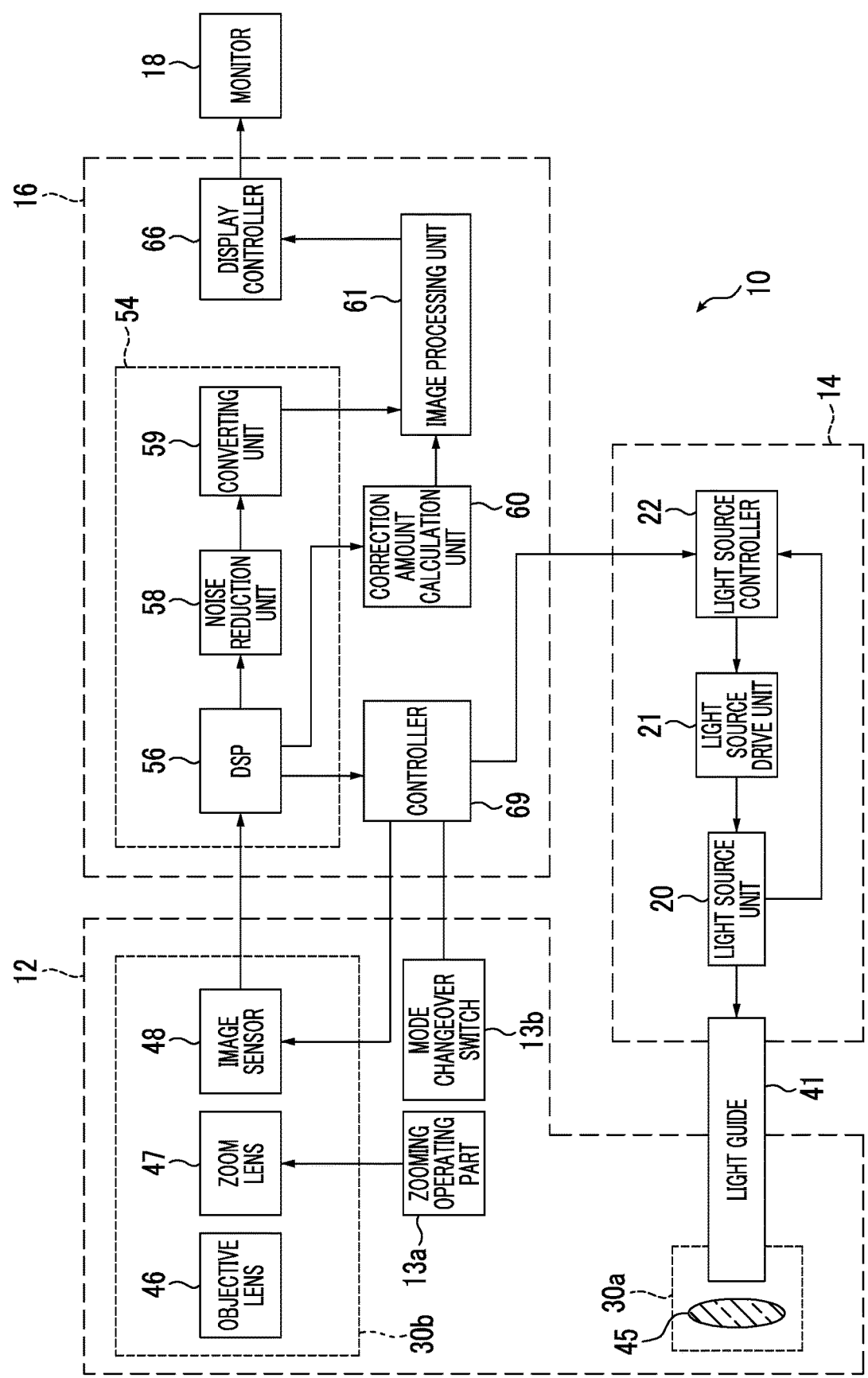
FIG. 2 is a block diagram conceptually illustrating the example of the endoscope system of the first embodiment of the invention.

FIG. 1 is a perspective view conceptually illustrating an example of an endoscope system of a first embodiment of the invention, and FIG. 2 is a block diagram conceptually illustrating an example of the endoscope system of the first embodiment of the invention.

As illustrated in FIG. 1, the endoscope system 10 includes an endoscope (hereinafter simply referred to as an endoscope) 12 that images an observation region within a living body (within a subject) that is an observation object, a processor device 16 that generates a display image of the observation region on the basis of image signals obtained by the imaging, a light source device 14 for endoscopes (hereinafter simply referred to as a light source device) that supplies illumination light, with which the observation region is irradiated, to the endoscope 12, and a monitor 18 that displays the display image. A console 19, which is operation input units, such as a keyboard and a mouse, is connected to the processor device 16.

The endoscope system 10 is capable of executing a normal observation mode for observing the observation region, and a blood vessel enhancement observation mode for enhancing and observing blood vessels that are present inside a mucous membrane of the observation region. The blood vessel enhancement observation mode is a mode for visualizing a pattern of the blood vessels as blood vessel information and performing diagnosis, such as differentiation of a malignant or benign tumor. In this blood vessel enhancement observation mode, the observation region is irradiated with illumination light including many components of light having a specific wavelength range in which the absorbance for hemoglobin in blood is high.

In the normal observation mode, a normal observation image suitable for observation of the entire observation region is generated as the display image. In the blood vessel enhancement observation mode, a blood vessel enhancement observation image suitable for observation of the pattern of the blood vessels is generated as the display image.

The endoscope 12 has an insertion part 12a to be inserted into the subject, an operating part 12b provided at a proximal end portion of the insertion part 12a, a bending part 12c provided on a distal end side of the insertion part 12a, and a distal end part 12d. By operating an angle knob 12e of the operating part 12b, the bending part 12c is bent. The distal end part 12d is directed in a desired direction as a result of the bending of the bending part 12c. In addition, the distal end part 12d is provided with a jet port (not illustrated) that jets air, water, or the like toward the observation object. Additionally, the operating part 12b is provided with a forceps port for inserting a treatment tool, an air/water supply button that is operated in a case where performing air supply or water supply from an air/water supply nozzle, a freeze button (not illustrated) for capturing a still image, a zooming operating part 13a, and a mode changeover switch 13b in addition to the angle knob 12e. The zooming operating part 13a is used for enlarging or reducing the observation object. The mode changeover switch 13b is used for switching a plurality of observation modes in a case where the endoscope system 10 has the plurality of observation modes.

Additionally, the endoscope 12 includes a universal cord 17 for connecting the endoscope 12 to the processor device 16 and the light source device 14.

A communication cable or light guide 41 (refer to FIG. 2) extending from the insertion part 12a is inserted through the universal cord 17, and a connector is attached to one end on the side of the processor device 16 and the light source device 14. The connector is a composite connector including a communication connector and a light source connector. The communication connector and the light source connector are detachably connected to the processor device 16 and the light source device 14, respectively. One end of the communication cable is disposed at the communication connector. An incident end of the light guide 41 is disposed at the light source connector.

As illustrated in FIG. 2, the light source device 14 includes a light source unit 20 having a plurality of light sources with different dominant wavelengths, a light source controller 22 that controls the light emission timing of the light source unit 20, light emission quantity, and the like, and a light source drive unit 21 that generates a driving current in accordance with a control signal of the light source controller 22 and supplies the driving current (driving signal) to each light source to make the light source emit light.

In the light source device 14, the light source controller 22 controls the light source drive unit 21 such that illumination light Ls (refer to FIG. 5) is radiated from the light source unit 20 to an object Ob (refer to FIG. 5) that is the observation object with a specific quantity of light. For example, even in a case where a distance Ld (refer to FIG. 5) of a distal end part 12d (refer to FIG. 5) of the endoscope and the object Ob (refer to FIG. 5) changes, the quantity of the illumination light Ls is controlled such that the brightness of an endoscopic image becomes constant. In this case, the quantity of the illumination light Ls is controlled such that the brightness value becomes constant, for example, using a brightness value obtained from a sensor signal of the image sensor 48.

In this case, the light source unit 20 is provided with photodetectors 91, 92, and 93 (refer to FIG. 5) as will be described below, and information on the quantities of light of the individual light sources detected by the photodetectors 91, 92, and 93 (refer to FIG. 5) is input to the light source controller 22, and the information on the quantities of light of the individual light sources is obtained. The light emission quantities of the light sources of the light source unit 20 are accurately and automatically controlled on the basis of the information on the quantities of light of the individual light sources and the brightness value of the image sensor 48.

The illumination light emitted from the light source unit 20 is incident on the light guide 41. The light guide 41 is built within the endoscope 12 and the universal cord 17 and propagates the illumination light up to the distal end part 12d of the endoscope 12. The universal cord 17 is a cord that connects the endoscope 12, and the light source device 14 and the processor device 16 together. In addition, multimode fiber can be used as the light guide 41. As an example, a fine-diameter fiber cable of which the core diameter is 105 μm, the clad diameter is 125 μm, and a diameter including a protective layer used as an outer cover is 0.3 to 0.5 mm can be used.

The distal end part 12d of the endoscope 12 is provided with an illumination optical system 30a and an imaging optical system 30b. The illumination optical system 30a has an illumination lens 45, and the illumination light is radiated to the observation object via the illumination lens 45. The imaging optical system 30b has an objective lens 46, a zoom lens 47, and an image sensor 48. The image sensor 48 images the observation object using reflected light or the like of the illumination light returning from the observation object via the objective lens 46 and the zoom lens 47. Scattered light, fluorescence emitted from the observation object, fluorescence resulting from a medicine administered to the observation object, in addition to the reflected light, or the like is included in the above-described reflected light or the like of the illumination light returning from the above-described observation object.

In addition, the zoom lens 47 is moved by operating the zooming operating part 13a. As a result, the observation object imaged using the image sensor 48 is enlarged or reduced and observed.

As the image sensor 48, for example, photoelectric conversion elements, such as a charge coupled device (CCD) sensor and a complementary metal-oxide semiconductor (CMOS) sensor, are used. In the image sensor 48 using a photoelectric conversion element, received light is photoelectrically converted, and a signal charge according to the quantity of the received light is accumulated as a sensor signal for each pixel. The signal charge for each pixel is converted into a voltage signal and is read from the image sensor 48. The voltage signal for each pixel read from the image sensor 48 is input to a digital signal processor (DSP) 56 as an image signal.

The image sensor 48 performs, for example, an accumulation operation in which a signal charge is accumulated in a pixel, and a reading operation in which the accumulated signal charge is read, within an acquisition period of one frame. The light source device 14 generates the illumination light in conformity with the timing of the accumulation operation of the image sensor 48, and make the illumination light incident on the light guide 41.

Figure 3:
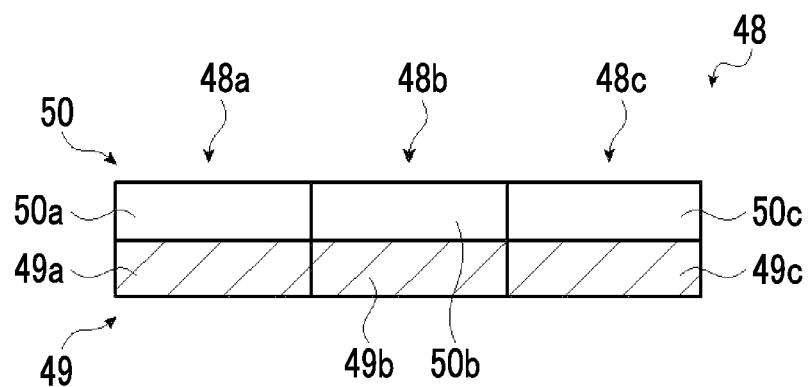
FIG. 3 is a schematic view illustrating an example of an image sensor of the endoscope system of the first embodiment of the invention.

As illustrated in FIG. 3, the image sensor 48 has a pixel unit 49 having a photoelectric conversion function, and a filter unit 50 having spectral sensitivity for a specific wavelength range, and a first element part 48a, a second element part 48b, and a third element part 48c are constituted by the pixel unit 49 and the filter unit 50. A signal charge is accumulated as a sensor signal as described above in the pixel unit 49 having the photoelectric conversion function.

In the image sensor 48, the first element part 48a has a first pixel 49a having the photoelectric conversion function, and a first filter 50a having the spectral sensitivity for a first color component. A first signal value of the first color component is obtained in the first element part 48a in accordance with the light incident on the image sensor 48.

The second element part 48b has a second pixel 49b having the photoelectric conversion function, and a second filter 50b having the spectral sensitivity for a second color component. A second signal value of the second color component is obtained in the second element part 48b in accordance with the light incident on the image sensor 48.

The third element part 48c has a third pixel 49c having the photoelectric conversion function, and a third filter 50c having the spectral sensitivity for a third color component. The third color component is a color other than the first color component and the second color component. A third signal value of the third color component is obtained in the third element part 48c in accordance with the light incident on the image sensor 48.

The image sensor 48 has, for example, a color sensor of a primary color system having a color filter in each pixel. The first filter 50a, the second filter 50b, and the third filter 50c are constituted of, for example, color filters. In this case, the first filter 50a, the second filter 50b, and the third filter 50c of the image sensor 48 are, for example, any of a red color filter (R color filter), a green color filter (G color filter), and a blue color filter (B color filter). The first element part 48a, the second element part 48b and the third element part 48c are appropriately determined in accordance with the above-described first color component, second color component, and third color component.

Among the individual pixels of the first pixel 49a, the second pixel 49b, and the third pixel 49c, a pixel having the R color filter is an R pixel, a pixel having the G color filter is a G pixel, and a pixel having the B color filter is a B pixel. As sensor signals of the image sensor 48, an R signal is obtained from the R pixel, a G signal is obtained from the G pixel, and a B signal is obtained from the B pixel. The R signal, the G signal, and the B signal are input to the DSP 56 as image signals.

In this way, since the image sensor 48 has, for example, three-color pixels of the R pixel, the G pixel, and the B pixel, an R image obtained by imaging the observation object with the R pixel, a G image obtained by imaging the observation object with the G pixel, and a B image obtained by imaging the observation object with the B pixel are simultaneously obtained in a case where the observation object is imaged using white light for the illumination light.

Figure 4:
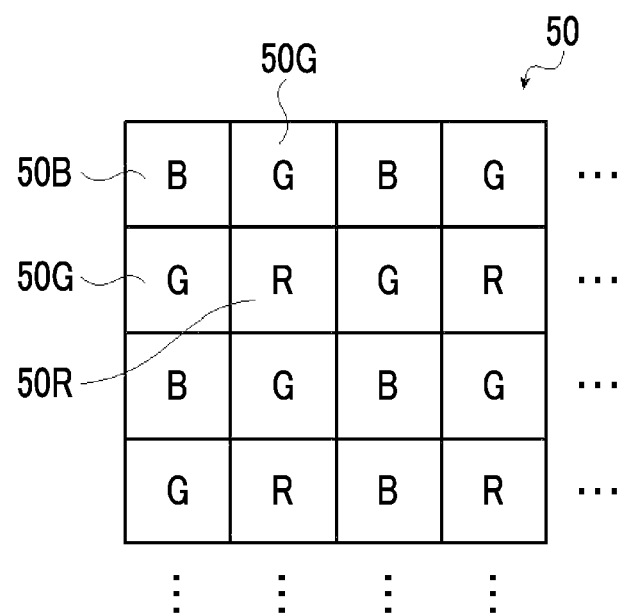
FIG. 4 is a schematic view illustrating an example of arrangement of color filters of the image sensor of the endoscope system of the first embodiment of the invention.

Although the arrangement of an R color filter 50R (refer to FIG. 4), a G color filter 50G (refer to FIG. 4), and a B color filter 50B (refer to FIG. 4) is not particularly limited, these color filters are disposed in a ratio of R:G:B=1:2:1 in consideration of visibility, for example, as illustrated in FIG. 4.

In addition, for example, a signal value of the above-described R signal is equivalent to a second signal value, a signal value of the G signal is equivalent to a first signal value, and a signal value of the B signal is equivalent to a third signal value.

In addition, although the color sensor of the primary color system has been exemplified as the image sensor 48, the image sensor is not limited to this, and a color sensor of a complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. The images obtained from the above-described individual color pixels in a case where the color sensor of the complementary color system is used can be converted into the B image, the G image, and the R image in a case where color conversion of complementary color and primary color is performed. Additionally, instead of the color sensor, a monochrome sensor that is not provided with the color filters can be used as the image sensor 48. In this case, the above-described individual images can be obtained by sequentially imaging the observation object using illumination light components in individual colors, such as BGR.

Additionally, a communication cable that performs communication of a driving signal for driving the image sensor 48 and the image signals output from the image sensor 48, and the light guide 41 that guides the illumination light supplied from the light source device 14 to an illumination window are inserted through the insertion part 12a illustrated in FIG. 1.

As illustrated in FIG. 2, the processor device 16 has an image acquisition unit 54, a correction amount calculation unit 60, an image processing unit 61, a display controller 66, and a controller 69. The processor device 16 is equivalent to a processor of the invention.

The image acquisition unit 54 obtains the image signals from the individual pixels of the image sensor 48 and acquires captured images in a plurality of colors, which are obtained by imaging the observation object using the image sensor 48. Specifically, the image acquisition unit 54 acquires a set of the B image, the G image, and the R image for each imaging frame. Additionally, the image acquisition unit 54 has the DSP 56, a noise reduction unit 58, and a converting unit 59, and performs various kinds of processing on the acquired captured images using these units. For example, the R signal, the G signal, and the B signal obtained as the sensor signals from the individual pixels of the image sensor 48 are output to the correction amount calculation unit 60 and the controller 69.

The DSP 56 performs various kinds of processing, such as defect correction processing, offset processing, gain correction processing, linear matrix processing, gamma conversion processing, demosaicing processing, and YC conversion processing, on the acquired captured images, as needed. Additionally, in the DSP 56, brightness values are obtained from the sensor signals of the image sensor 48 input as the image signals. In addition, for example, the G signal may be used as a brightness value.

The defect correction processing is the processing of correcting the pixel value of a pixel corresponding to a defective pixel of the image sensor 48.

The offset processing is the processing of reducing a dark current component from the images subjected to the defect correction processing and setting an accurate zero level.

The gain correction processing is the processing of adjusting a signal level of each image by multiplying the images subjected to the offset processing by a gain.

The linear matrix processing is the processing of enhancing color reproducibility on the images subjected to the offset processing, and the gamma conversion processing is the processing of adjusting the brightness or saturation of the image after the linear matrix processing.

The demosaicing processing (also referred to as equalization processing or synchronization processing) is the processing of interpolating the pixel value of a missing pixel and is performed on the images after the gamma conversion processing. The missing pixel is a pixel with no pixel value because pixels in other colors are disposed in the image sensor 48 due to the arrangement of color filters. For example, since the B image is an image obtained by imaging the observation object in the B pixel, there is no pixel value in pixels at positions corresponding to the G pixel and the R pixel of the image sensor 48. In the demosaicing processing, the pixel values of the pixels at the positions of the G pixel and the R pixel of the image sensor 48 are generated by interpolating the B image.

The YC conversion processing is the processing of converting the images after the demosaicing processing into a luminance channel Y, a color difference channel Cb, and a color difference channel Cr.

The noise reduction unit 58 performs noise reduction processing using, for example, a moving average method, a median filter method, or the like, on the luminance channel Y, the color difference channel Cb, and the color difference channel Cr.

The converting unit 59 re-converts the luminance channel Y, the color difference channel Cb, and the color difference channel Cr after the noise reduction processing into images in respective colors of BGR.

The correction amount calculation unit 60 performs correction for maintaining the hue of the endoscopic image, and calculates correction coefficients to be described below or stores the correction coefficients.

The image processing unit 61 performs color conversion processing, color enhancement processing, and structure enhancement processing on the B image, the G image, and the R image, equivalent to one imaging frame, subjected to the above various kinds of processing to generate an observation image. In the color conversion processing, 3×3 matrix processing, grayscale conversion processing, three-dimensional look-up table (LUT) processing, or the like is performed on the images in the individual colors of BGR. The color enhancement processing is the processing of enhancing the colors of an image, and the structure enhancement processing is the processing of enhancing, for example, the tissue or structure of the observation object, such as blood vessels and pit patterns.

The display controller 66 sequentially acquires observation images from the image processing unit 61, converts the acquired observation images into a format suitable for display, and sequentially outputs and displays the converted images to and on the monitor 18. Accordingly, a doctor or the like can observe the observation object using still images or moving images of the observation images.

The controller 69 has, for example, a central processing unit (CPU), and performs overall control of the endoscope system 10, such as emission timing of the illumination light and synchronous control of an imaging frame. Additionally, in a case where the endoscope system 10 has the plurality of observation modes, the controller 69 switches the illumination light via the light source controller 22 by receiving an operation input from the mode changeover switch 13b. Accordingly, the observation mode is switched.

The processor device 16 is electrically connected to the monitor 18 and the console 19. The monitor 18 outputs and displays the observation images, accompanying image information, and the like if necessary. The console 19 functions as a user interface that receives an input operation, such as a function setting. In addition, an external recording unit (not illustrated) that records the images, the image information, and the like may be connected to the processor device 16.

Figure 5:
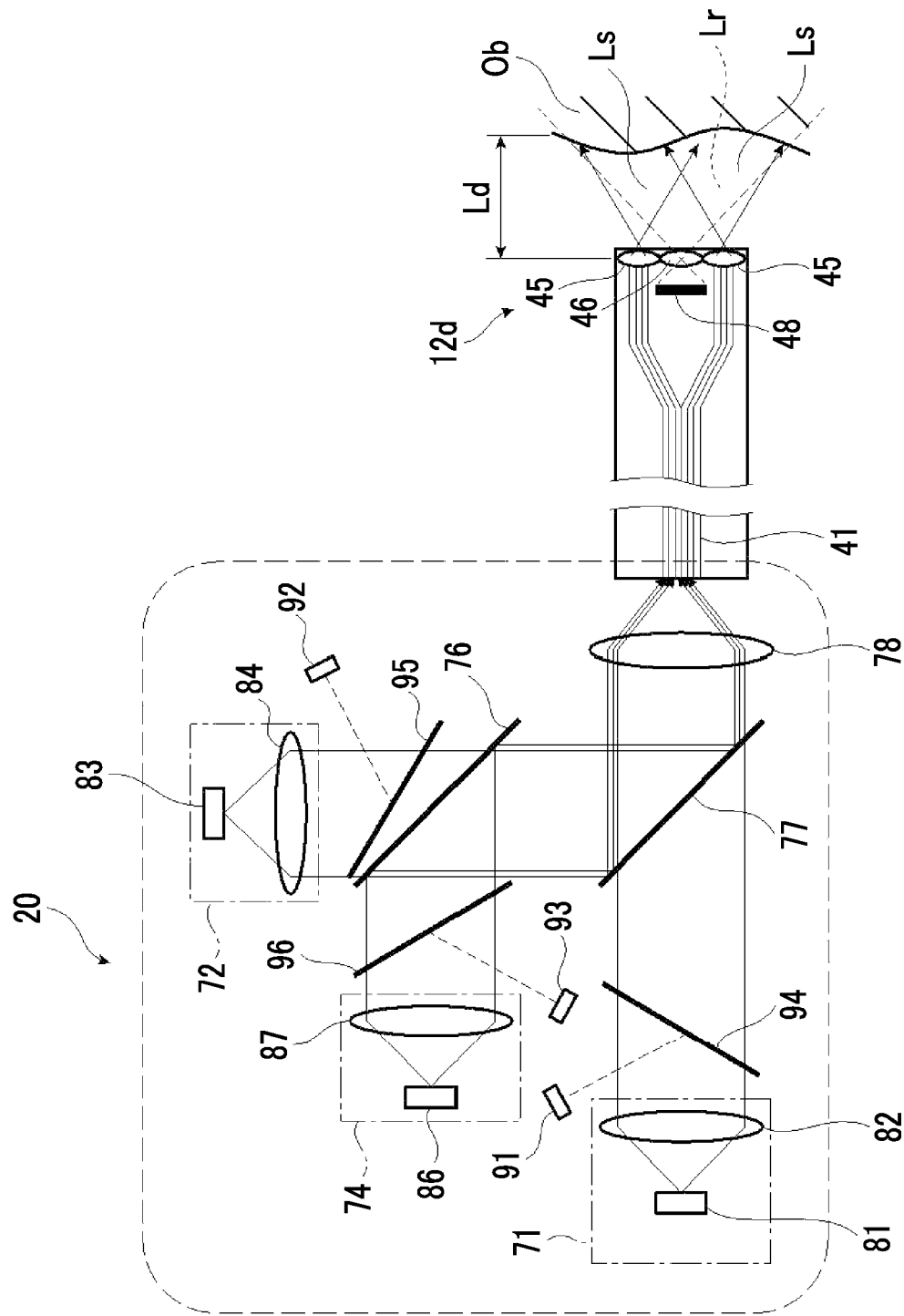
FIG. 5 is a schematic view illustrating an example of a light source unit of the endoscope system of the first embodiment of the invention.

Hereinafter, the configuration and the operation of the light source device 14 will be described in more detail. FIG. 5 is a schematic view illustrating an example of the light source unit of the endoscope system of the first embodiment of the invention.

As illustrated in FIG. 5, the light source unit 20 of the light source device 14 has a first light source 71, a second light source 72, and an additional light source 74. The first light source 71, the second light source 72, and the additional light source 74 can be respectively and independently controlled. Additionally, the light source unit 20 includes a cooling member, such as a heat sink, that cools light emitting elements of individual light sources of the first light source 71, the second light source 72, and the additional light source 74.

In the light source device 14, the light emitted from the light source unit 20 passes through the light guide 41, and is radiated to the object Ob as the illumination light Ls. Reflected light Lr of the illumination light Ls radiated to the object Ob is incident on the image sensor 48 via the objective lens 46.

First light emitted by the first light source 71 is incident on the light guide 41 via a multiplexing member 77 and a lens 78 that allow the first light to pass therethrough.

A beam splitter 94 is provided between the first light source 71 and the multiplexing member 77. A portion of the first light emitted by the first light source 71 is reflected in a predetermined ratio by the beam splitter 94. The light reflected by the beam splitter 94 is received by a photodetector 91. The light source controller 22 automatically and accurately controls the light emission quantity of the first light of the first light source 71 using the quantity of the light detected by the photodetector 91.

Second light emitted by the second light source 72 is incident on the light guide 41 via a multiplexing member 76 and the multiplexing member 77, which transmit the second light, and the lens 78.

A beam splitter 95 is provided between the second light source 72 and the multiplexing member 76. A portion of the second light emitted by the second light source 72 is reflected in a predetermined ratio by the beam splitter 95. The light reflected by the beam splitter 95 is received by a photodetector 92. The light source controller 22 automatically and accurately controls the light emission quantity of the second light of the second light source 72 using the quantity of the light detected by the photodetector 92.

Light emitted by the additional light source 74 is incident on the light guide 41 via the multiplexing member 76, the multiplexing member 77, which transmits the light emitted by the additional light source 74, and the lens 78.

A beam splitter 96 is provided between the additional light source 74 and the multiplexing member 76. A portion of the light emitted by the additional light source 74 is reflected in a predetermined ratio by the beam splitter 96. The light reflected by the beam splitter 96 is received by a photodetector 93. The light source controller 22 automatically and accurately controls the light emission quantity of the light of the additional light source 74 using the quantity of the light detected by the photodetector 93.

The multiplexing member 76 and the multiplexing member 77 are, for example, dichroic mirrors, dichroic prisms, or the like. The lens 78 is for narrowing the light from the light source unit 20 to make the narrowed light incident on the light guide 41.

The photodetectors 91, 92, and 93 are, for example, photomultiplier tubes using a photoelectric effect, photoconductive elements, such as CdS or PbS, using electric resistance changes caused by photoirradiation, photoelectromotive force type photodiodes using a pn junction of or a semiconductor, or the like.

The first light source 71 includes a light emitting element 81 that emits the first light including two color components with mutually different wavelengths, and a lens 82 that shapes the first light emitted by the light emitting element 81 into parallel light or the like. The light emitting element 81 is, for example, a semiconductor element, such as a light emitting diode (LED) or an LD having an emission spectrum including the first color component and the second color component out of the two color components with mutually different wavelengths.

The first light source 71 is, for example, a light source that emits light (hereinafter referred to as green light) having a green component including two color components with mutually different wavelengths, in which the first color component is green and the second color component is red. Light of one color is used as light of two colors. The green light is also referred to as light showing green.

The second light source 72 includes a light emitting element 83 that emits the second light as light of the color other than the above-described two color components with mutually different wavelengths, and a lens 84 that shapes the second light emitted by the light emitting element 83 into parallel light or the like. The light emitting element 83 is, for example, a semiconductor element, such as an LED or an LD.

Out of the two color components with mutually different wavelengths in the first light source 71, for example, in a case where the first color component is green and the second color component is red, the second light source 72 emits light (hereinafter referred to as blue light) including a blue component. The blue light is also referred to as light showing blue.

In the first light source 71, blue light in which the first color component is blue and the second color component is green may be used. In this case, a light source that emits light (hereinafter referred to as red light) including a red component is used as the second light source 72. The red light is also referred to as light showing red.

The two color components with mutually different wavelengths mean that the number of separable color components is two. Here, as described above, the blue light is light having a wavelength of about 440 nm or more and less than about 490 nm. The green light is light having a wavelength of about 490 nm or more and less than about 600 nm. The red light is light having a wavelength of about 600 nm or more and less than about 680 nm. For example, light having a wavelength range of 490 nm to 700 nm includes the above-described green light and red light. For example, light having a wavelength range of 440 nm to 600 nm includes the above-described blue light and green light.

In two or more light sources with different dominant wavelengths, the different dominant wavelengths mean that peak wavelengths of light emitted by individual light sources are not the same wavelength, and central wavelengths are not the same wavelength in a case where there is no peak wavelength. The same range of the peak wavelengths or the central wavelengths is appropriately determined in accordance with the specification or the like of the endoscope system 10.

The additional light source 74 emits, for example, light (hereinafter referred to as purple light) including a purple component. The additional light source 74 includes a light emitting element 86, and a lens 87 that shapes the purple light emitted by the light emitting element 86 into parallel light or the like. The light emitting element 86 is, for example, a semiconductor element, such as an LED or an LD. The purple light emitted by the additional light source 74 is incident on the light guide 41 via the multiplexing member 77 that transmits the purple light and the multiplexing member 76 that reflects the purple light. The purple component of the purple light is received by the B pixel in the image sensor 48. For this reason, the reflected light of the purple light contributes to the B image together with the reflected light of the blue light, or the like.

In the normal observation mode, the light source controller 22 turns the first light source 71 and the second light source 72 and turns off the additional light source 74. Meanwhile, in the blood vessel enhancement observation mode, the light source controller 22 turns on all the first light source 71, the second light source 72, and the additional light source 74.

In a case where the first light source 71 emits the green light in which the first color component is green and the second color component is red and the second light source 72 emits the blue light, in the normal observation mode, light including the green light and the red light emitted by the first light source 71 and the blue light emitted by the second light source 72 are multiplexed to generate broadband white light. Meanwhile, in the blood vessel enhancement observation mode, mixed light in which purple light having a high absorbance for hemoglobin in blood is mixed with the white light is generated. In addition, in the blood vessel enhancement observation mode, the light source controller 22 lowers the ratio of the quantity of the blue light such that the purple light becomes more dominant than the blue light.

Figure 6:
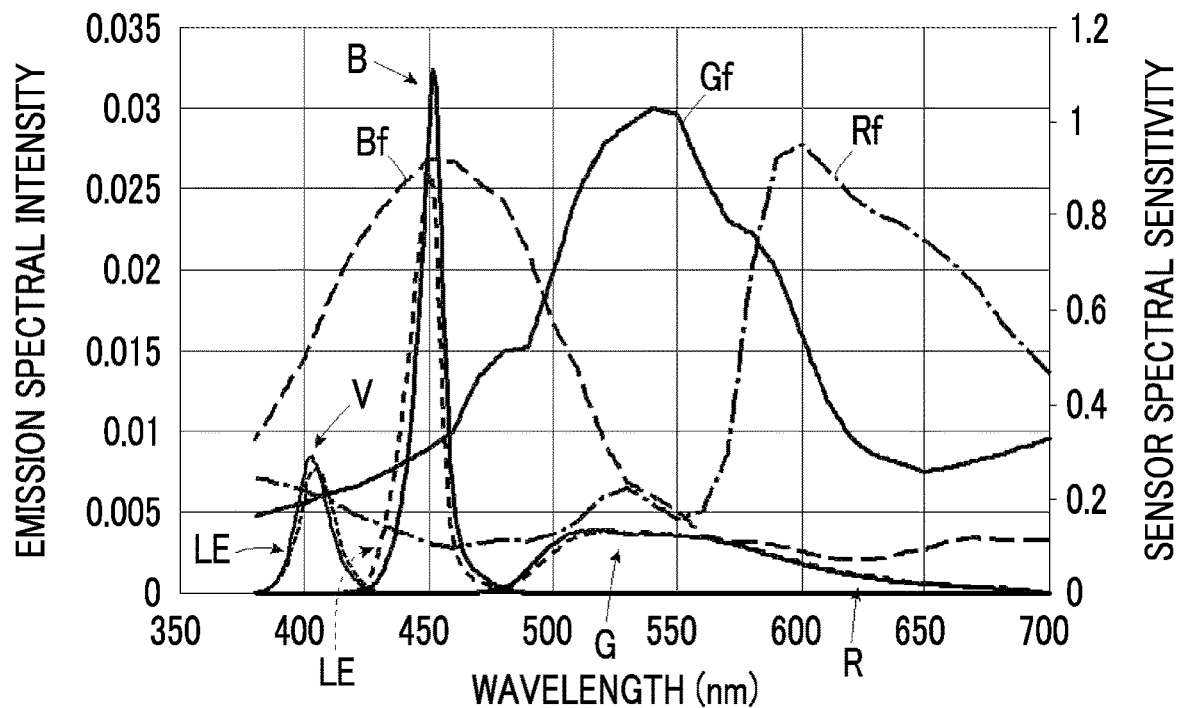
FIG. 6 is a graph illustrating an example of the emission spectrum of the light source unit and the spectral sensitivity of the image sensor in the endoscope system of the first embodiment of the invention.

In the light source device 14 of the above-described configuration, the light emitted from the light source unit 20 of the light source device 14, that is, the illumination light Ls (refer to FIG. 5), which passes through the light guide 41 of the endoscope 12 and is emitted from the distal end part 12d of the endoscope, has, for example, an emission spectrum LE illustrated in FIG. 6.

Figure 7:
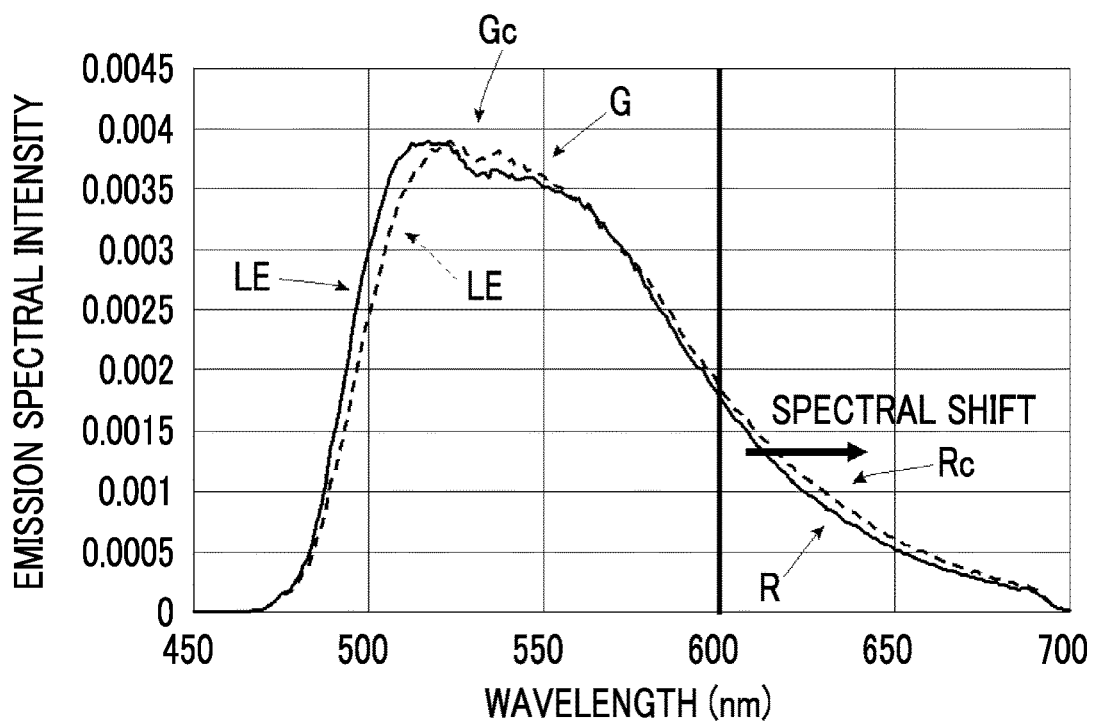
FIG. 7 is a graph illustrating a wavelength shift caused by a light quantity change in the emission spectrum of the light source unit of the endoscope system of the first embodiment of the invention.

Here, FIG. 6 is a graph illustrating an example of the emission spectrum of the light source unit and the spectral sensitivity of the image sensor in the endoscope system of the first embodiment of the invention, and FIG. 7 is a graph illustrating a wavelength shift caused by a light quantity change in the emission spectrum of the light source unit of the endoscope system of the first embodiment of the invention. FIG. 7 is a graph illustrating a range including a green color component Gc and a red color component Rc as color components having a wavelength of 450 nm to 700 nm in the emission spectrum LE of FIG. 6, in an enlarged manner.

In addition, in the emission spectrum LE illustrated in FIG. 6, symbol V represents the purple light, symbol B represents the blue light, symbol G represents the green light, and symbol R represents the red light. Additionally, in the emission spectrum LE illustrated in FIG. 6, a solid line shows that the quantity of light is relatively low, and a dashed line shows that the quantity of light is relatively high.

In the emission spectrum LE illustrated in FIG. 6, a peak wavelength is present near the wavelength of 400 nm and a peak wavelength is present near the wavelength of 450 nm. The peak wavelength near the wavelength of 400 nm is based on the purple light emitted by the additional light source 74, and the peak wavelength near the wavelength of 450 nm is based on the blue light emitted by the second light source 72.

Light having a wavelength of 470 nm to 700 nm is based on the green light emitted by the first light source 71, and includes green and red as color components.

The emission spectrum LE illustrated in FIG. 6 represents substantially white light. In the endoscope system 10, the observation object is imaged with the reflected light Lr of the illumination light Ls having the emission spectrum LE including the blue light, the green light, and the red light by using the image sensor 48 having a spectral sensitivity characteristic illustrated in FIG. 6. Symbol Bf illustrated in FIG. 6 represents a spectral sensitivity for the light showing blue. Symbol Gf represents a spectral sensitivity for the light showing green. Symbol Rf represents a spectral sensitivity for the light showing red. The spectral sensitivity Bf and the spectral sensitivity Gf have an overlapping wavelength range, and the spectral sensitivity Gf and the spectral sensitivity Rf have an overlapping wavelength range. The spectral sensitivity is not limited to these.

The image sensor 48 has the first element part 48a, the second element part 48b, and the third element part 48c as described above. For example, the first element part 48a has the spectral sensitivity Gf for the light showing green. The second element part 48b has the spectral sensitivity Rf for the light showing red. The third element part 48c has the spectral sensitivity Bf for the light showing blue.

Additionally, the first light source 71 may be configured to have a light emitting diode having a light emission peak between the peak wavelength of the spectral sensitivity of the first element part 48a and the peak wavelength of the spectral sensitivity of the second element part 48b. In this case, in a case where the first element part 48a has the spectral sensitivity Gf and the second element part 48b has the spectral sensitivity Rf, a light emitting diode having a light emission peak in a wavelength of 550 to 600 nm is used. In a case where the first element part 48a has the spectral sensitivity Bf and the second element part 48b has the spectral sensitivity Gf, a light emitting diode having a light emission peak in a wavelength of 450 to 550 nm is used.

Figure 8:
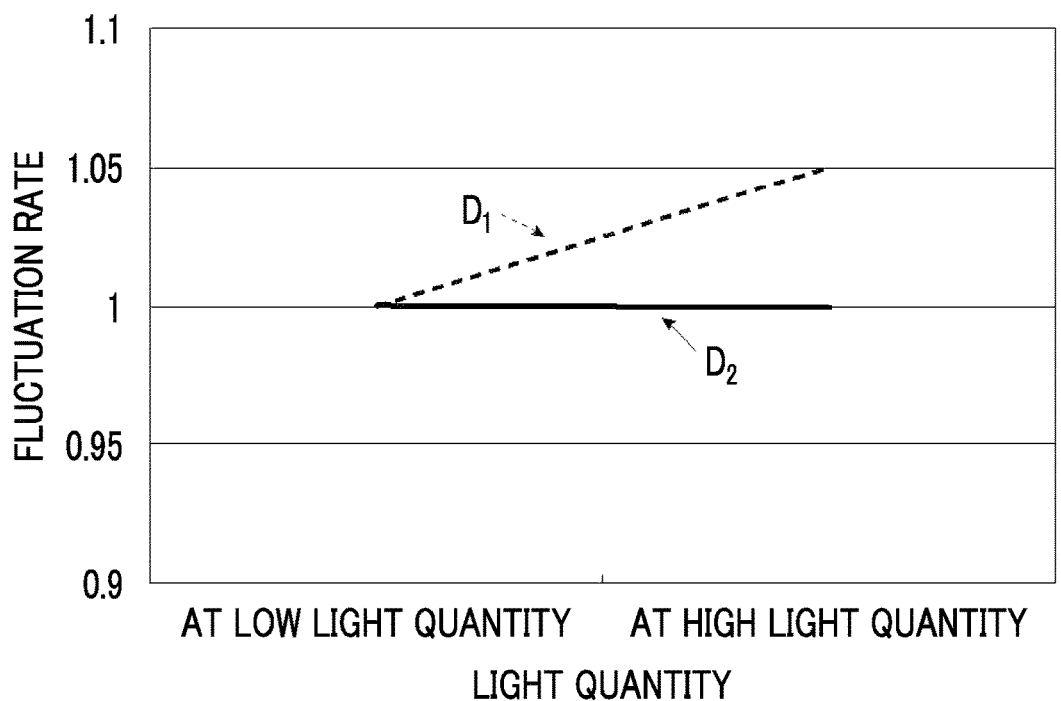
FIG. 8 is a graph illustrating an example of fluctuations of signal ratios in the image sensor of the endoscope system of the first embodiment of the invention.

Here, in a case where the quantity of light changes, as illustrated in FIGS. 6 and 7, the wavelength of the emission spectrum LE shifts. In the emission spectrum LE illustrated in FIG. 6, the green light including the color components of green and red is emitted from one first light source 71. Therefore, in a case where the light quantity ratio of the green color component Gc and the red color component Rc changes as illustrated in FIG. 7 due to the wavelength shift of the emission spectrum LE caused by the light quantity change, the light quantity ratio of the green color component Gc and the red color component Rc is not constant. As a result, in the image sensor 48, as illustrated in FIG. 8, due to the light quantity change, particularly a signal ratio $D_1$ between the signal value of the red light and the signal value of the green light is not constant but may shift.

Accordingly, the hue of the endoscopic image of the observation object obtained via the image sensor 48 shifts due to the light quantity change. That is, the white balance of the endoscopic image collapses. In order to suppress the shift of the hue caused by the light quantity change and making the hue constant irrespective of the quantity of light, the following processing is carried out by the processor device 16.

In addition, regarding the green light and the blue light, the wavelength shift of the emission spectrum does not occur or the wavelength shift is small. As illustrated in FIG. 8, a signal ratio $D_2$ between the signal value of the blue light and the signal value of the green light is constant irrespective of the quantity of light.

The observation object is imaged using the light emitted from at least one first light source 71 of the light source unit 20, and the first signal value of the first color component obtained by the first element part 48a of the image sensor 48 and the second signal value of the second color component obtained by the second element part 48b are obtained in the processor device 16. The processor device 16 calculates a signal ratio between the first signal value and the second signal value, and sets the signal ratio to a predetermined set value by changing at least one signal value out of the first signal value and the second signal value.

In the image sensor 48, the first signal value of the first color component is obtained in the first element part 48a, the second signal value of the second color component is obtained in the second element part 48b, and a third signal value of light of a color other than the two color components is obtained in the third element part 48c.

Then, the first signal value and the second signal value are output from the DSP 56 to the correction amount calculation unit 60. In the correction amount calculation unit 60, the signal ratio is obtained between the first signal value and the second signal value, and the signal ratio is set to the predetermined set value by changing at least one signal value out of the first signal value and the second signal value.

Additionally, the signal ratio may be set to the predetermined set value by changing at least one signal value among the first signal value, the second signal value, and the third signal value in accordance with the quantity of light. In this case, the first signal value, the second signal value, or the third signal value, which changes in accordance with the quantity of light, is determined, the changing value is obtained as a correction coefficient, and the correction coefficient is stored in the correction amount calculation unit 60.

In the correction amount calculation unit 60, for example, the signal ratio is set to 1 that is the predetermined set value, a correction coefficient of the signal value of the red light or a correction coefficient of the signal value of the green light, in which the above-described signal ratio becomes 1 with respect to the signal ratio $D_1$ between the signal value of the red light and the signal value of the green light as illustrated in FIG. 8, is obtained, and the correction coefficient is stored in the correction amount calculation unit 60. Then, in the image processing unit 61, the correction coefficient is called from the correction amount calculation unit 60, and correction processing is performed on the G image or the R image for one imaging frame using the correction coefficient. In this case, by changing the signal value of the red light or the signal value of the green light, as described above, the signal ratio can be set to the predetermined set value, for example, the signal ratio can be set to 1.

Additionally, a brightness value is calculated using at least one of the first signal value and the second signal value and the quantity of light of the first light source 71 is specified on the basis of the brightness value. Also, the signal ratio may be set to the predetermined set value by changing at least one signal value out of the first signal value and the second signal value in accordance with the quantity of light. In this case, in the correction amount calculation unit 60, the first signal value or the second signal value, which changes in accordance with the quantity of light, is determined, the changing value is obtained as a correction coefficient, and the correction coefficient is stored in the correction amount calculation unit 60.

Additionally, a brightness value is calculated using at least among the first signal value, the second signal value, or the third signal value, and the quantity of light of the first light source 71 is specified on the basis of the brightness value. Also, the signal ratio may be set to the predetermined set value by changing at least one signal value among the first signal value, the second signal value, and the third signal value in accordance with the quantity of light with one signal value among the first signal value, the second signal value, and the third signal value as a reference value. Being set to such a set value is also referred to as white balance processing.

In this case, in the correction amount calculation unit 60, the first signal value, the second signal value, or the third signal value that is used as the reference value is determined, the first signal value, the second signal value, or the third signal value that changes in accordance with the quantity of light is determined, the changing value is obtained as a correction coefficient, and the correction coefficient is stored in the correction amount calculation unit 60.

In addition, in the above description, one signal value is used as the reference value, but the invention is not limited to this. Additionally, the signal ratio may be set to the predetermined set value by changing at least one signal value among the first signal value, the second signal value, and the third signal value in accordance with the quantity of light without setting the reference value.

Through the white balance processing, the hue of the endoscopic image cannot be made constant irrespective of the quantity of light. Hereinafter, the white balance processing will be described. In this case, a case where the B signal, the G signal, and the R signal of the endoscopic image is obtained by the image sensor 48 will be described as an example. Additionally, the G signal is used as a reference of the white balance processing.

First, at the time of manufacturing the endoscope system, white plate imaging is actually performed at a reference light quantity point $P_0$, and signal ratios $B(P_0)/G(P_0)$ and $R(P_0)/G(P_0)$ in the reference light quantity point P0 are obtained. In this case, the signal ratios are actually measured values.

White balance gains in the reference light quantity point P0 are inverse numbers of the signal ratios $G(P_0)/B(P_0)$ and $G(P_0)/R(P_0)$ in the reference light quantity point $P_0$.

Moreover, at the time of manufacturing the endoscope system, fluctuation rates $\Delta(B/G)(P)$ and $\Delta(R/G)(P)$ of the signal ratios caused by the wavelength shift of the emission spectrum of the endoscope emission by the light quantity change are obtained.

A method of obtaining the fluctuation rates Δ(B/G)(P) and Δ(R/G)(P) of the signal ratios expressed by the following equations is as follows.

First, in an arbitrary light quantity P, signal ratios actually measured using the white plate directly may be used, or the wavelength shift of the emission spectrum of the illumination light Ls emitted from the light source unit 20 may be actually measured by a spectrometer, and signal ratios calculated using the spectral sensitivity of a known image sensor may be used. In addition, the sensor signals can be obtained by integrating the spectral sensitivity of the image sensor and the emission spectrum.

$$\Delta(B/G)(P) \equiv \frac{B(P)/G(P)}{B(P_0)/G(P_0)},$$

$$\Delta(R/G)(P) \equiv \frac{R(P)/G(P)}{R(P_0)/G(P_0)}$$

Equation 1

Here, $\Delta(B/G)(P_0)=1$ and $\Delta(R/G)(P_0)=1$ are satisfied. The signal ratios in the arbitrary light quantity P are as follows.

$$B(P_0)/G(P_0)\cdot\Delta(B/G)(P), R(P_0)/G(P_0)\cdot\Delta(R/G)(P)$$

Equation 2

As illustrated in the following equation, the inverse numbers of the signal ratios in the above-described arbitrary light quantity P become light-quantity-dependent white balance gains.

$$\frac{G(P_0)}{B(P_0)}\frac{1}{\Delta(B/G)(P)},$$

$$\frac{G(P_0)}{R(P_0)}\frac{1}{\Delta(R/G)(P)}$$

Equation 3

Here, since portions $G(P_0)/B(P_0)$ and $G(P_0)/R(P_0)$ of the above-described equation are the white balance gains of the reference light quantity point $P_0$, inverse numbers Iv of signal ratio fluctuation rates of the sensor signals, that is, $Iv=1/(\Delta(B/G)(P))$ and $Iv=1/(\Delta(R/G)(P))$ become light-quantity-dependent gain correction coefficients.

At the time of actually using the endoscope system, the white balance gains of the reference light quantity point $P_0$ and the light-quantity-dependent gain correction coefficients are stored in the correction amount calculation unit 60 of the endoscope system 10. The white balance processing is executed by multiplying the B signal and the R signal obtained by imaging the observation object by the light-quantity-dependent gain correction coefficients.

At the time of the white plate imaging, all the signals in the arbitrary light quantity P are adjusted to G(P).

$$G(P) \rightarrow G(P)$$

$$B(P) \rightarrow \frac{G(P_0)}{B(P_0)}\frac{1}{\Delta(B/G)(P)}\cdot B(P) = G(P)$$

$$R(P) \rightarrow \frac{G(P_0)}{R(P_0)}\frac{1}{\Delta(R/G)(P)}\cdot R(P) = G(P)$$

Equation 4

A specific example of the white balance processing for making the hue of the endoscopic image constant irrespective of the quantity of light will be described. In this case, a case where the B signal, the G signal, and the R signal of the endoscopic image is obtained by the image sensor 48 will be described as an example.

Figure 9:
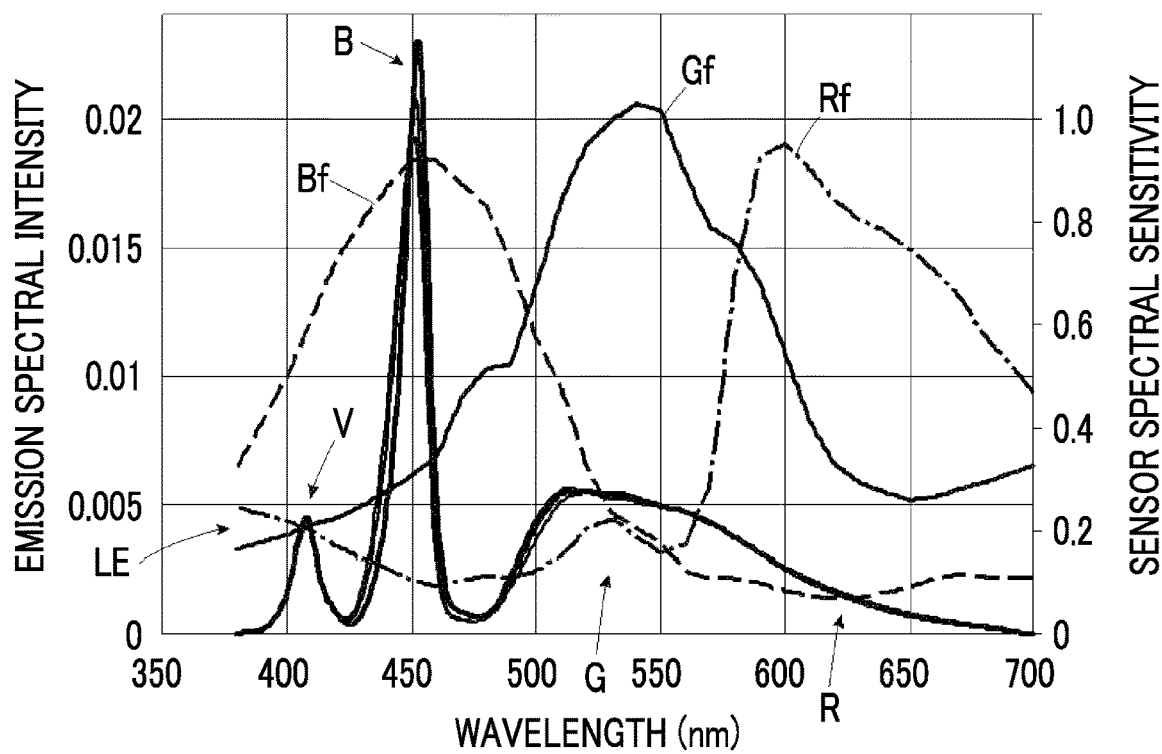
FIG. 9 is a graph illustrating an example of a wavelength shift caused by a light quantity change in the emission spectrum of the light source unit and the spectral sensitivity of the image sensor in the endoscope system of the first embodiment of the invention.
Figure 10:
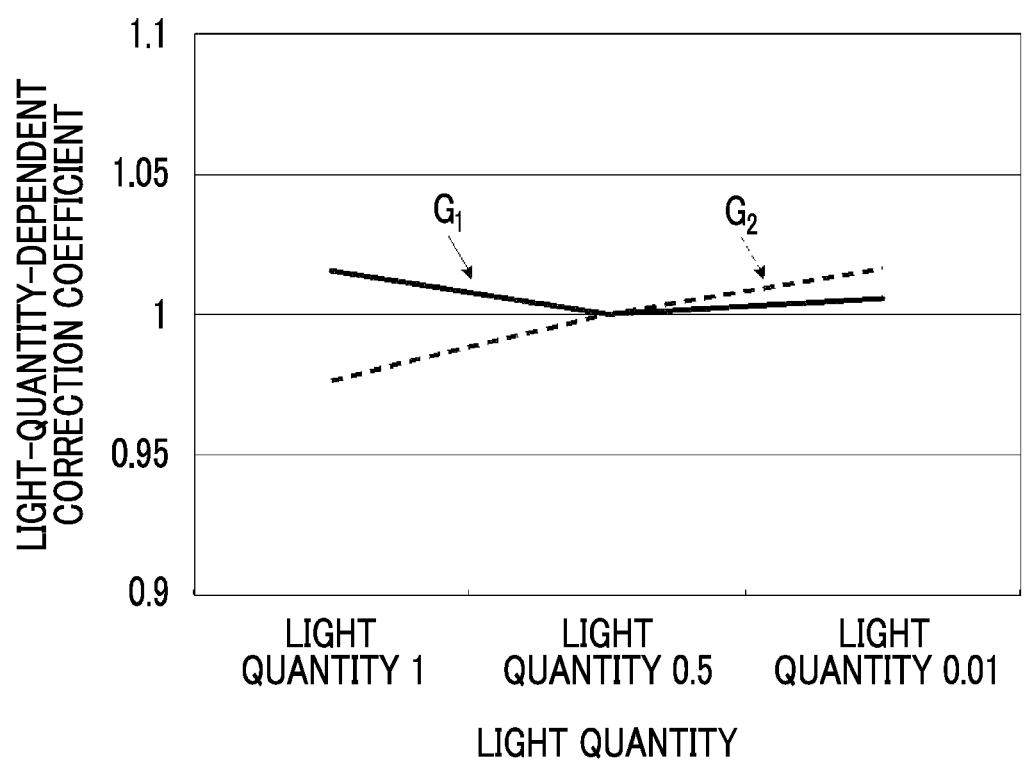
FIG. 10 is a graph illustrating an example of signal correction coefficients of the endoscope system of the first embodiment of the invention.

FIG. 9 is a graph illustrating an example of a wavelength shift caused by a light quantity change in the emission spectrum of the light source unit and the spectral sensitivity of the image sensor in the endoscope system of the first embodiment of the invention, and FIG. 10 is a graph illustrating an example of signal correction coefficients of the endoscope system of the first embodiment of the invention.

First, signal values in a case where the illumination light Ls is radiated to the white plate with individual light quantities including light quantity of 1, light quantity of 0.5, and light quantity of 0.01 from the light source unit 20 are assumed as shown as in the following Table 1. Here, at this time, the signal values are unknown to an adjustment worker who performs the white balance processing.

TABLE 1

| Sensor Signal | Light Quantity 1 | Light Quantity 0.5 | Light Quantity 0.01 |
|---|---|---|---|
| B Signal | 710.4 | 667.7 | 617.0 |
| G Signal | 880.6 | 814.8 | 757.1 |
| R Signal | 367.8 | 332.5 | 303.9 |

In order to perform the white balance processing, the adjustment worker may actually adjust only the signal values with the white plate by using light quantity 0.5 of Table 1 as a reference light quantity point. Signal values of light quantity 1 and light quantity of 0.01 are still unknown to the adjustment worker. Next, signal ratios are calculated from individual signals of light quantity 0.5 of Table 1, and inverse numbers of the signal ratios are taken to obtain gains shown in the following Table 2. Naturally, in this stage, gains of light quantity 1 and light quantity of 0.01 are unknown.

TABLE 2

| Gain | Light Quantity 1 | Light Quantity 0.5 | Light Quantity 0.01 |
|---|---|---|---|
| $G_0/B_0$ | — | 1.220 | — |
| $G_0/G_0$ | — | 1.000 | — |
| $R_0/B_0$ | — | 2.451 | — |

Next, the emission spectrum LE illustrated in FIG. 9 is actually measured. Additionally, signal ratios in individual light quantities are obtained using the spectral sensitivity of the image sensor 48 illustrated in FIG. 9. "B/G" of the following Table 3 shows the signal ratio of the B signal and the G signal, and "R/G" represents the signal ratio of the R signal and the G signal. Although the signal values of the light quantity of 1 and the light quantity of 0.01 are unknown to the adjustment worker, the signal ratios of the light quantity of 1 and light quantity of 0.01 become clear by this measurement. The measurement of the emission spectrum is a simpler method (imaging is not included) using only the illumination light than the measurement using the white plate, and only the latter method may be carried out regarding light quantity 1 and light quantity of 0.01.

TABLE 3

| Signal Ratio | Light Quantity 1 | Light Quantity 0.5 | Light Quantity 0.01 |
|---|---|---|---|
| B/G | 0.807 | 0.819 | 0.815 |
| R/G | 0.418 | 0.408 | 0.401 |

Next, the signal ratio fluctuation rates Δ(B/G) and Δ(R/G) may be obtained by calculation. The signal ratio fluctuation rates are standardized, for example, at the reference light quantity point $P_0$ of a light quantity of 0.5.

TABLE 4

| Signal Ratio Fluctuation Rate | Light Quantity 1 | Light Quantity 0.5 | Light Quantity 0.01 |
|---|---|---|---|
| Δ(B/G) | 0.985 | 1.000 | 0.995 |
| Δ(R/G) | 1.024 | 1.000 | 0.984 |

Next, the light-quantity-dependent gain correction coefficients 1/(Δ(B/G)) and 1/(Δ(R/G)) are obtained by calculation. The light-quantity-dependent gain correction coefficients are inverse numbers Iv of the signal ratio fluctuation rates. Accordingly, for example, as illustrated in FIG. 10, the light-quantity-dependent gain correction coefficients can be obtained. Symbol $G_1$ of FIG. 10 represents the light-quantity-dependent gain correction coefficient 1/(Δ(B/G)), and symbol $G_2$ represents the light-quantity-dependent gain correction coefficient 1/(Δ(R/G)).

TABLE 5

| Light-Quantity-Dependent Correction Coefficient | Light Quantity 1 | Light Quantity 0.5 | Light Quantity 0.01 |
|---|---|---|---|
| 1/(Δ(B/G)) | 1.016 | 1.000 | 1.005 |
| 1/(Δ(R/G)) | 0.977 | 1.000 | 1.016 |

Next, the light-quantity-dependent white balance gains are obtained by calculation. The light-quantity-dependent white balance gains are values of the product of the above-described light-quantity-dependent gain correction coefficients and the gain in the reference light quantity point.

TABLE 6

| Light-Quantity-Dependent White Balance Gain | Light Quantity 1 | Light Quantity 0.5 | Light Quantity 0.01 |
|---|---|---|---|
| G(P)/B(P) | 1.240 | 1.220 | 1.227 |
| G(P)/R(P) | 2.394 | 2.451 | 2.491 |

At the time of actual use of the endoscope system, by multiplying the light-quantity-dependent white balance gains of Table 6 acquired by the adjustment by the sensor signals in the individual light quantities of Table 1 acquired in a case where the endoscope system is actually used, the white balance can be taken regarding the B signal, the G signal, and the R signal that are obtained in the image sensor 48. Although the signal values of light quantity 1 of Table 1 and Table 7 and light quantity of 0.01 are not clear to the adjustment worker, the white balance of the signal values is reliably taken at the time of actual use of the endoscope system. As a result, the white balance processing can be carried out on the endoscopic image, the endoscopic image with constant hue irrespective of the quantity of light can be obtained, and more accurate diagnosis is possible.

TABLE 7

| Sensor Signal | Light Quantity 1 | Light Quantity 0.5 | Light Quantity 0.01 |
|---|---|---|---|
| B Signal | 880.6 | 814.8 | 757.1 |
| G Signal | 880.6 | 814.8 | 757.1 |
| R Signal | 880.6 | 814.8 | 757.1 |

As illustrated in the above-described FIG. 6, the spectral sensitivity Bf and the spectral sensitivity Gf have the overlapping wavelength range, and the spectral sensitivity Gf and the spectral sensitivity Rf have the overlapping wavelength range. However, it is possible to obtain a higher-purity endoscopic image with no color mixture as the range of the wavelength of the spectral sensitivity of the image sensor 48 is narrower and the overlapping wavelength range is narrower. In a case where the overlapping wavelength range is narrow, the above-described signal ratios tend to shift due to the wavelength shift of the emission spectrum, and a change in hue tends to occur. However, even in a case where the overlapping wavelength range is narrow, the endoscopic image can be made constant irrespective of the quantity of light by virtue of the above-described white balance processing. In this way, even in a case where the range of the wavelength of the spectral sensitivity of the image sensor 48 is narrow, the above-described white balance processing is effective.

In addition, the configuration of the light source unit 20 is not limited to the configuration illustrated in the above-described FIG. 5.

Figure 11:
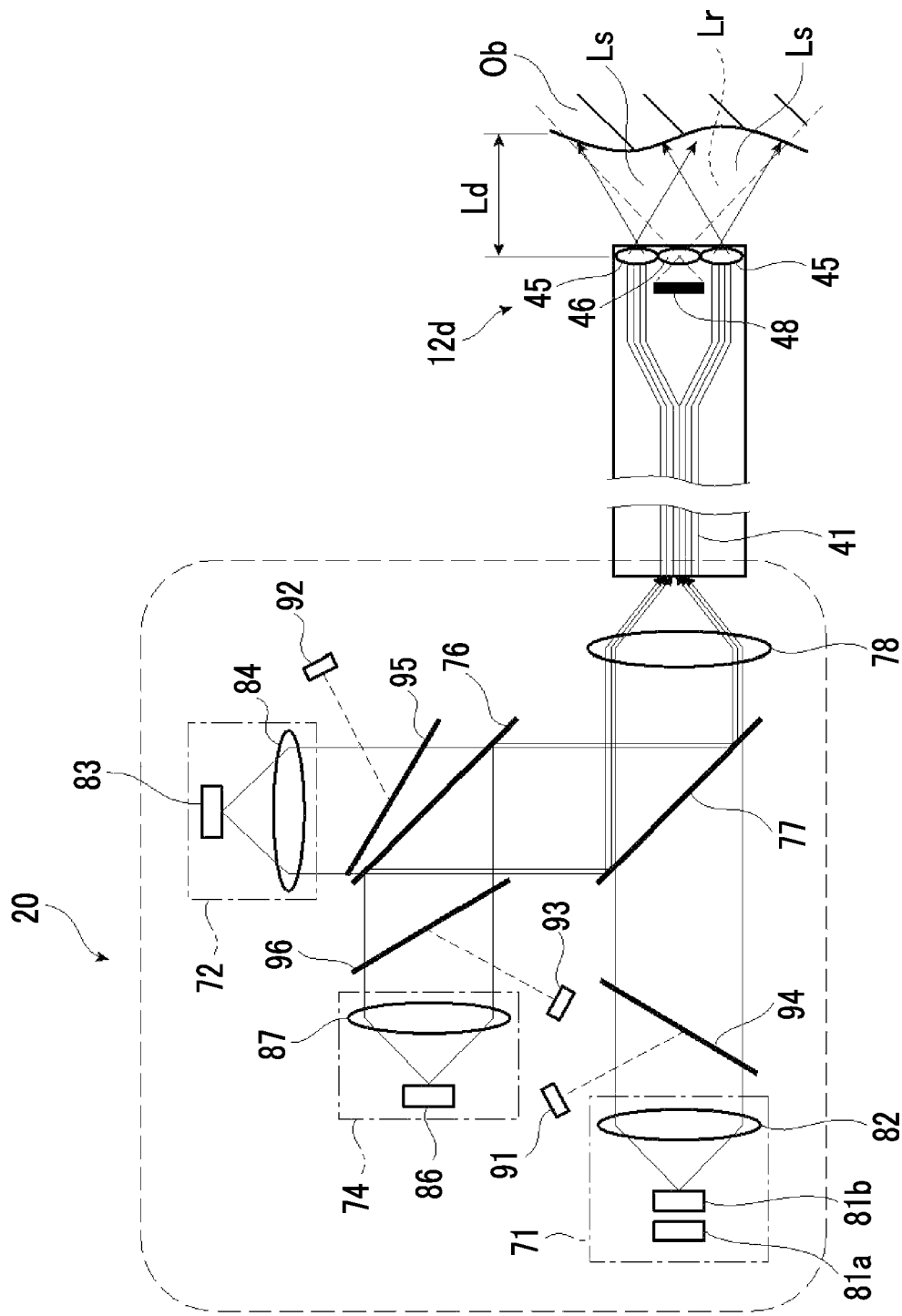
FIG. 11 is a schematic view illustrating a modification example of the example of the light source unit of the endoscope system of the first embodiment of the invention.

FIG. 11 is a schematic view illustrating a modification example of the example of the light source unit of the endoscope system of the first embodiment of the invention.

Since a light source unit 20 illustrated in FIG. 11 is different from the light source unit 20 illustrated in FIG. 5 in the configuration of the first light source 71 and the other configuration thereof is the same as that of the light source unit 20 illustrated in FIG. 5, the detailed description thereof will be described.

The first light source 71 illustrated in FIG. 11 has a light emitting element 81a that emits excitation light, and a fluorescent body 81b that emits light including two color components with mutually different wavelengths as the excitation light emitted by the light emitting element 81a is incident thereon.

In the first light source 71, for example, the excitation light emitted by the light emitting element 81a is blue light having a peak in about 445 nm, and the light emitted by the fluorescent body 81b is broadband green light includes the red component in addition to the green component. In addition to this, the first light source 71 may emit broadband blue light including the green component in addition to the blue component by changing the wavelength of the excitation light emitted by the light emitting element 81a, and the fluorescent body 81b.

Second Embodiment

Next, a second embodiment will be described.

Figure 12:
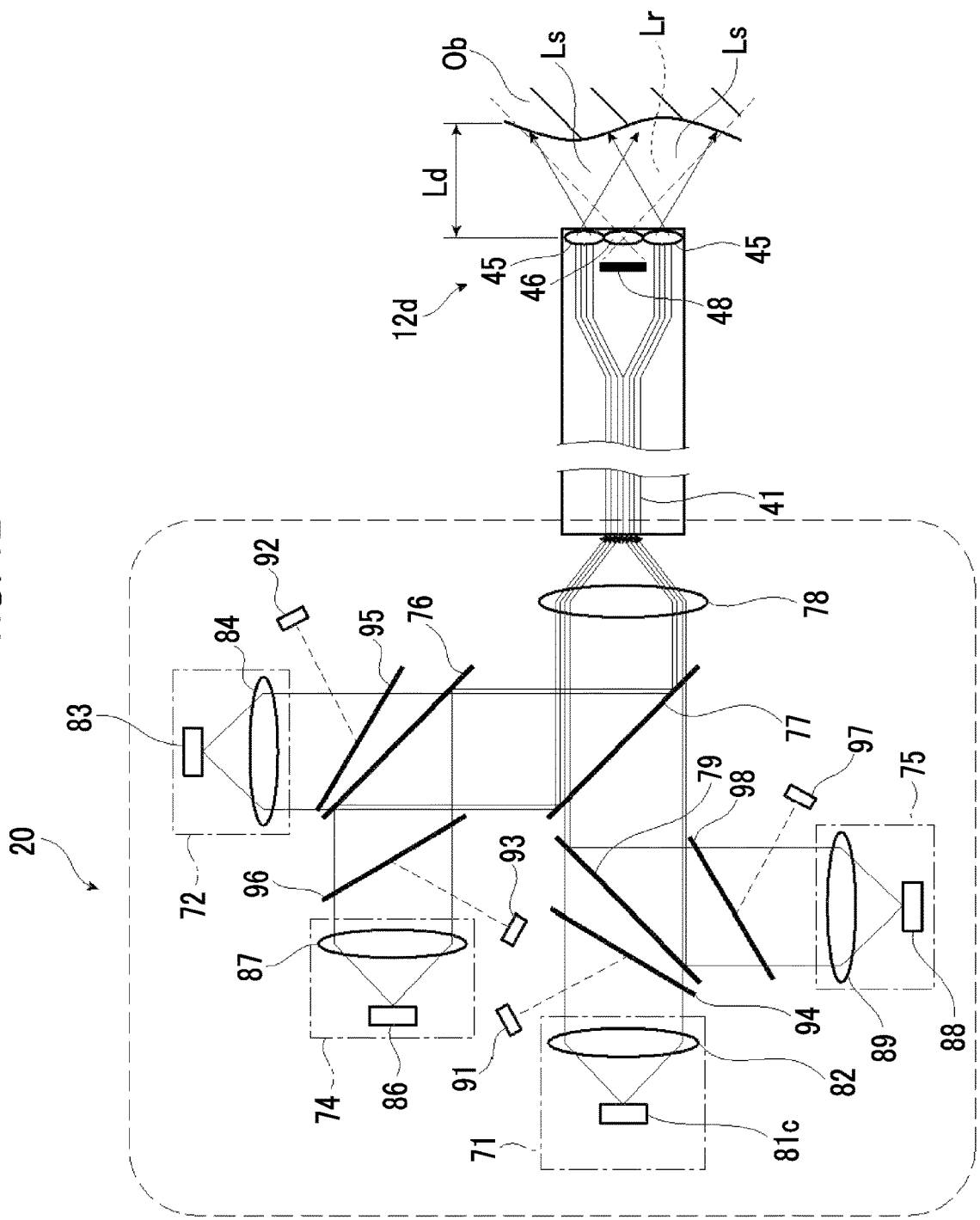
FIG. 12 is a schematic view illustrating an example of a light source unit of an endoscope system of a second embodiment of the invention.

FIG. 12 is a schematic view illustrating an example of a light source unit of an endoscope system of the second embodiment of the invention. The second embodiment is different in the configuration of the light source unit.

Since the light source unit 20 illustrated in FIG. 12 is different from the light source unit 20 illustrated in FIG. 5 in the configuration of light sources and the other configuration thereof is the same as that of the light source unit 20 illustrated in FIG. 5, the detailed description thereof will be described.

The light source unit 20 illustrated in FIG. 12 has a third light source 75. In the light source unit 20 illustrated in FIG. 5, the light including the two color components with mutually different wavelengths is emitted from the first light source 71. However, in the light source unit 20 illustrated in FIG. 12, light of the first color component is emitted from the first light source 71, and light of the second color component is emitted as third light from the third light source 75.

A multiplexing member 79 is provided between the first light source 71 and the multiplexing member 77. The multiplexing member 79 transmits the light emitted by the first light source 71. The multiplexing member 79 multiplexes the light of the first color component emitted by the first light source 71 and the light of the second color component emitted by the third light source 75, and guides the multiplexed light to the multiplexing member 77. The first light source 71, the second light source 72, the third light source 75, and the additional light source 74 can be respectively and independently controlled.

The third light source 75 includes a light emitting element 88 that emits the light of the second color component as the third light, and a lens 89 that shapes the light emitted by the light emitting element 88 into parallel light or the like. The light emitting element 88 is, for example, a semiconductor element, such as an LED or an LD. The third light emitted by the third light source 75 is incident on the light guide 41 via the multiplexing member 79 and the multiplexing member 77 that allow the third light to be transmitted therethrough.

A beam splitter 98 is provided between the third light source 75 and the multiplexing member 79. A portion of the third light emitted by the third light source 75 is reflected in a predetermined ratio by the beam splitter 98. The light reflected by the beam splitter 98 is received by a photodetector 97. The light source controller 22 automatically and accurately controls the light emission quantity of the third light of the third light source 75 using the quantity of the light detected by the photodetector 97.

The multiplexing member 79 has the same configuration as the multiplexing member 76 and the multiplexing member 77, and is, for example, a dichroic mirror, a dichroic prism, or the like.

The photodetector 97 has the same configuration as the above-described photodetectors 91, 92, and 93.

A light emitting element 81c of the first light source 71 emits, for example, the green light as the light of the first color component. The light emitting element 88 of the third light source 75 emits, for example, the red light as the light of the second color component.

Additionally, the light emitting element 81c of the first light source 71 may emit, for example, the blue light as the light of the first color component, the light emitting element 88 of the third light source 75 may emit, for example, the green light as the light of the second color component, and the second light source 72 may emit the red light.

Figure 13:
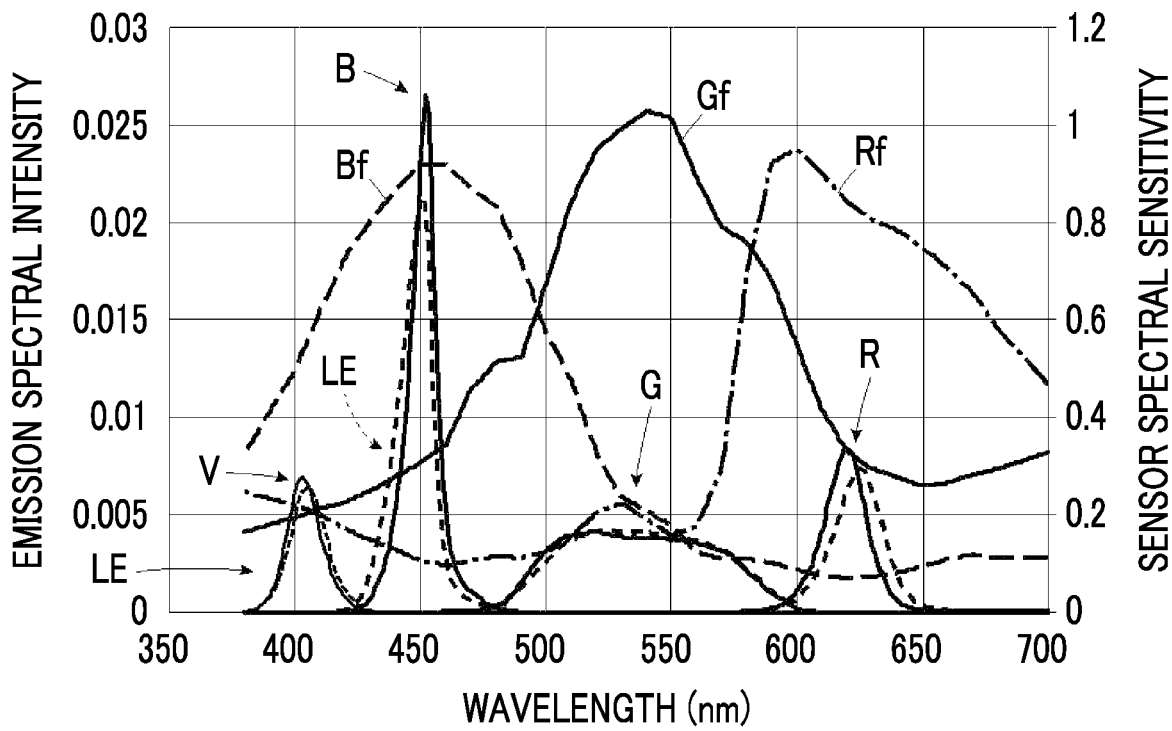
FIG. 13 is a graph illustrating an example of the emission spectrum of the light source unit and the spectral sensitivity of an image sensor in the endoscope system of the second embodiment of the invention.
Figure 14:
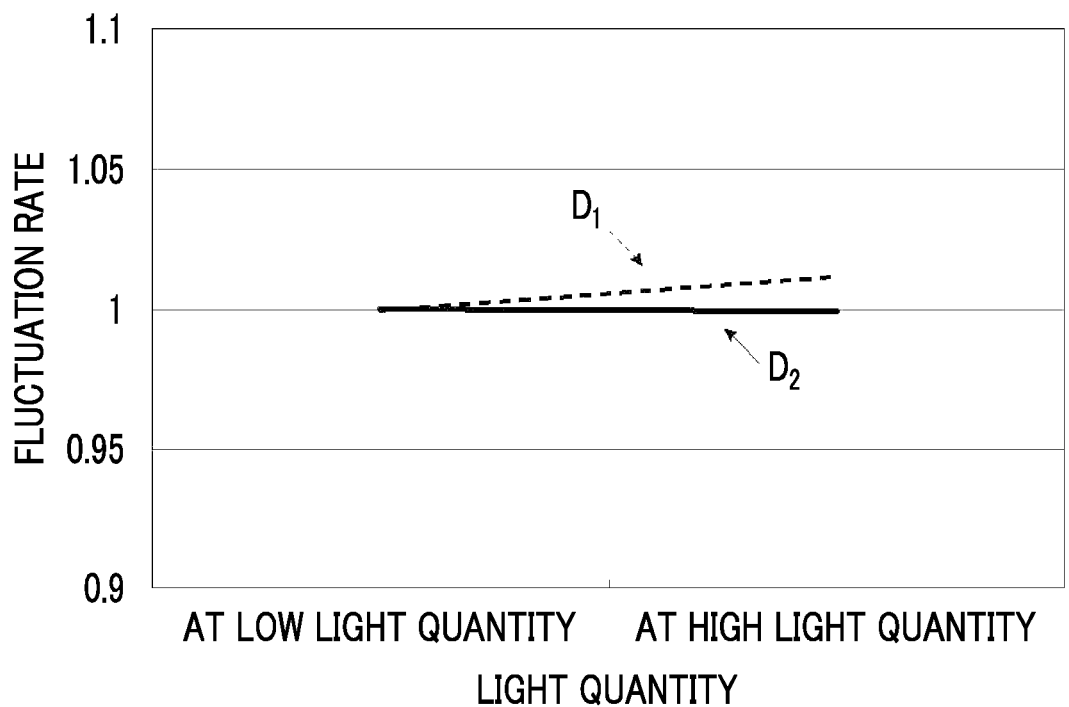
FIG. 14 is a graph illustrating an example of fluctuations of signal ratios in the image sensor of the endoscope system of the second embodiment of the invention.

FIG. 13 is a graph illustrating an example of the emission spectrum of the light source unit and the spectral sensitivity of an image sensor in the endoscope system of the second embodiment of the invention, and FIG. 14 is a graph illustrating an example of fluctuations of signal ratios in the image sensor of the endoscope system of the second embodiment of the invention. In the emission spectrum LE illustrated in FIG. 13, a solid line shows that the quantity of light is relatively low, and a dashed line shows that the quantity of light is relatively high.

In the emission spectrum LE and the spectral sensitivity of the image sensor 48, which are illustrated in FIG. 13, the same configuration as the emission spectrum LE and the spectral sensitivity of the image sensor 48, which are illustrated in FIG. 6, will be designated by the same reference signs, and the detailed description thereof will be omitted.

The spectral sensitivity of the image sensor 48 illustrated in FIG. 13 is the same as the spectral sensitivity of the image sensor 48 illustrated in FIG. 6.

The emission spectrum LE illustrated in FIG. 13 is different from the emission spectrum LE illustrated in FIG. 6 in that a peak wavelength is present near the wavelength of 630 nm, and that there is light having a wavelength of 500 to 600 nm, and is the same as the emission spectrum LE illustrated in FIG. 6 except these.

The peak wavelength near the wavelength of 630 nm is based on the red light emitted by the third light source 75. The light having a wavelength of 500 to 600 nm is based on the green light emitted by the first light source 71.

The light source unit 20 illustrated in FIG. 13 also has the wavelength shift of the emission spectrum LE. For this reason, as illustrated in FIG. 14, particularly the signal ratio $D_1$ between the signal value of the red light and the signal value of the green light is not constant but shift. In addition, the signal ratio $D_2$ between the signal value of the blue light and the signal value of the green light is constant irrespective of the quantity of light.

Even in such a case, as described above, a signal ratio can be set to a predetermined set value by obtaining the correction coefficients, and the hue of the endoscopic image can be made constant irrespective of the quantity of light. In this way, in a case where the wavelength shift of the emission spectrum LE occurs, the hue of the endoscopic image can be made constant without being limited to the configuration of the light source unit 20.

The invention is basically configured as described above. Although the endoscope system of the invention has been described above in detail, it is natural that the invention is not limited to the above-described embodiment, and various improvements and modifications may be made without departing from the scope of the invention.

EXPLANATION OF REFERENCES

10: endoscope system
12: endoscope
12a: insertion part
12b: operating part
12c: bending part
12d: distal end part
12e: angle knob
13a: zooming operating part
13b: mode changeover switch
14: light source device
16: processor device
17: universal cord
18: monitor
19: console
20: light source unit
21: light source drive unit
22: light source controller
30a: illumination optical system
30b: imaging optical system
41: light guide
45: illumination lens
46: objective lens
47: zoom lens
48: image sensor
48a: first element part
48b: second element part
48c: third element part
49: pixel unit
49a: first pixel 49b: second pixel
49c: third pixel
50: filter unit
50B: B color filter
50G: G color filter
50R: R color filter
50a: first filter
50b: second filter
50c: third filter
54: image acquisition unit
58: noise reduction unit
59: converting unit
60: correction amount calculation unit
61: image processing unit
66: display controller
69: controller
71: first light source
72: second light source
74: additional light source
75: third light source
76: multiplexing member
77: multiplexing member
78: lens
79: multiplexing member
81, 81a, 81b, 81c, 83, 86, 88: light emitting element
82, 84, 87, 89: lens
91 92, 93, 97: photodetector
94 95, 96, 98: beam splitter
Bf, Gf, Rf: spectral sensitivity
$D_1$, $D_2$: signal ratio
$G_1$, $G_2$: light-quantity-dependent gain correction coefficient
Gc: green color component
LE: emission spectrum
Lr: reflected light
Ld: distance
Ls: illumination light
Ob: object
Rc: red color component

What is claimed is:

1. An endoscope system comprising:
a light source unit including at least one first light source that emits light including two color components with mutually different wavelengths;
an image sensor having at least a first element part that has a spectral sensitivity for a first color component and a second element part that has a spectral sensitivity for the second color component out of the two color components of the first light source; and
a processor that images an observation object using the light emitted from the light source unit and obtains a first signal value of the first color component obtained in the first element part of the image sensor, and a second signal value of the second color component obtained in the second element part of the image sensor,
wherein the processor calculates a first signal ratio between the first signal value and the second signal value, calculates a brightness value using at least one of the first signal value and the second signal value of the image sensor, specifies a quantity of light of the light source unit on the basis of the brightness value, and sets the first signal ratio to a predetermined set value by changing at least one signal value out of the first signal value and the second signal value obtained from the image sensor in accordance with the quantity of light.

2. The endoscope system according to claim 1,
wherein the light source unit has at least one second light source that emits light of a color other than the two color components,
wherein the image sensor has at least a third element part that has a spectral sensitivity for the light of the color other than the two color components, and
wherein the processor obtains a third signal value of the light of the color other than the two color components obtained in the third element part of the image sensor.

3. The endoscope system according to claim 2,
wherein the light source unit has one first light source and one second light source,
wherein the image sensor has the first element part, the second element part, and the third element part, and
wherein the processor obtains the first signal value, the second signal value, and the third signal value that are respectively obtained in the first element part, the second element part, and the third element part of the image sensor, and the processor calculates a second signal ratio between the first signal value and the third signal value.

4. The endoscope system according to claim 3,
wherein the processor calculates the brightness value from at least one of the first signal value, the second signal value, and the third signal value of the image sensor, specifies the quantity of light of the light source unit on the basis of the brightness value, and sets either one of the first signal ratio and the second signal ratio to the predetermined set value by changing at least one signal value out of the first signal value, the second signal value, and the third signal value in accordance with the quantity of light.

5. The endoscope system according to claim 3,
wherein the processor sets either one of the first signal ratio and the second signal ratio to the predetermined set value by changing at least one signal value out of the first signal value, the second signal value, and the third signal value obtained from the image sensor in accordance with the quantity of light with one signal value among the first signal value, the second signal value, and the third signal value as a reference value.

6. The endoscope system according to claim 3,
wherein the light of the color other than the two color components is light showing blue, and
wherein, out of the two color components, the first color component is green and the second color component is red.

7. The endoscope system according to claim 3,
wherein the light of the color other than the two color components is light showing red, and
wherein, out of the two color components, the first color component is blue and the second color component is green.

8. The endoscope system according to claim 1,
wherein the light source unit has, as the first light source, a light source that emits light including the first color component showing green and the second color component showing red, or a light source that emits light including the first color component showing blue and the second color component showing green.

9. The endoscope system according to claim 1,
wherein the light source unit has, as the first light source, a light source that emits light including the first color component showing green and the second color component showing red, and a light source that emits light including the first color component showing blue and the second color component showing green.

10. The endoscope system according to claim 1,
wherein the first light source has a light emitting element that emits excitation light, and a fluorescent body that emits light including the first color component and the second color component with the excitation light.

11. The endoscope system according to claim 1,
wherein the first light source has a light emitting diode including an emission spectrum including the first color component and the second color component.

12. The endoscope system according to claim 11,
wherein the first light source has a light emitting diode having a light emission peak between a peak wavelength of the spectral sensitivity of the first element part and a peak wavelength of the spectral sensitivity of the second element part.

13. The endoscope system according to claim 1,
wherein the image sensor has a range where the spectral sensitivity of the first element part and the spectral sensitivity of the second element part overlap each other.

14. An endoscope system comprising:
a light source unit including at least one first light source that emits light including two color components with mutually different wavelengths;
an image sensor having at least a first element part that has a spectral sensitivity for a first color component and a second element part that has a spectral sensitivity for the second color component out of the two color components of the first light source; and
a processor that images an observation object using the light emitted from the at least one first light source of the light source unit, obtains a first signal value of the first color component obtained in the first element part of the image sensor, and a second signal value of the second color component obtained in the second element part, and calculates a signal ratio between the first signal value and the second signal value,
wherein in the first light source, a light quantity ratio between the first color component and the second color component changes depending on the quantity of light of the light to be emitted, and
wherein the processor calculates a brightness value using at least one of the first signal value and the second signal value of the image sensor, specifies the quantity of light of the first light source on the basis of the brightness value, and changes at least one signal value out of the first signal value and the second signal value obtained from the image sensor such that the signal ratio has a predetermined set value in accordance with the quantity of light.

15. The endoscope system according to claim 4,
wherein the light of the color other than the two color components is light showing blue, and
wherein, out of the two color components, the first color component is green and the second color component is red.

16. The endoscope system according to claim 4,
wherein the light of the color other than the two color components is light showing red, and
wherein, out of the two color components, the first color component is blue and the second color component is green.

17. The endoscope system according to claim 2,
wherein the light source unit has, as the first light source, a light source that emits light including the first color component showing green and the second color component showing red, or a light source that emits light including the first color component showing blue and the second color component showing green.

18. The endoscope system according to claim 2,
wherein the light source unit has, as the first light source, a light source that emits light including the first color component showing green and the second color component showing red, and a light source that emits light including the first color component showing blue and the second color component showing green.

19. The endoscope system according to claim 2,
wherein the first light source has a light emitting element that emits excitation light, and a fluorescent body that emits light including the first color component and the second color component with the excitation light.

* * * * *